US008852666B2

(12) United States Patent
Heittiarachchy et al.

(10) Patent No.: US 8,852,666 B2
(45) Date of Patent: Oct. 7, 2014

(54) PROTECTIVE HYDROCOLLOID FOR ACTIVE INGREDIENTS

(75) Inventors: Navagnana S. Heittiarachchy, Fayetteville, AR (US); Bruno H. Leueberger, Rheinfelden (CH); Ilankovan Paraman, Fayetteville, AR (US); Christian Schaefer, Rheinfelden (DE)

(73) Assignee: DSM IP Assets B.V., Heerlen (NL)

( * ) Notice: Subject to any disclaimer, the term of this patent is extended or adjusted under 35 U.S.C. 154(b) by 18 days.

(21) Appl. No.: 12/593,995

(22) PCT Filed: Mar. 22, 2008

(86) PCT No.: PCT/EP2008/002315
§ 371 (c)(1),
(2), (4) Date: Apr. 16, 2010

(87) PCT Pub. No.: WO2008/119482
PCT Pub. Date: Oct. 9, 2008

(65) Prior Publication Data
US 2010/0197568 A1  Aug. 5, 2010

(51) Int. Cl.
| | |
|---|---|
| A23J 1/00 | (2006.01) |
| A23L 2/66 | (2006.01) |
| A23L 1/305 | (2006.01) |
| A23L 1/172 | (2006.01) |
| A23J 3/14 | (2006.01) |
| A23J 1/12 | (2006.01) |
| A23L 1/00 | (2006.01) |
| A23L 1/275 | (2006.01) |
| C07K 14/415 | (2006.01) |
| A23L 1/302 | (2006.01) |
| A23K 1/16 | (2006.01) |
| A23L 1/303 | (2006.01) |
| A23J 3/34 | (2006.01) |

(52) U.S. Cl.
CPC ............ *A23J 3/346* (2013.01); *A23V 2002/00* (2013.01); *A23L 2/66* (2013.01); *A23L 1/3053* (2013.01); *A23L 1/172* (2013.01); *A23J 3/14* (2013.01); *A23J 1/125* (2013.01); *A23L 1/0029* (2013.01); *A23L 1/2751* (2013.01); *C07K 14/415* (2013.01); *A23L 1/302* (2013.01); *A23K 1/1631* (2013.01); *A23L 1/303* (2013.01)
USPC ........................................................ 426/656

(58) Field of Classification Search
USPC ........................................................ 426/656
See application file for complete search history.

(56) References Cited

U.S. PATENT DOCUMENTS

2004/0191365 A1* 9/2004 Leuenberger .................. 426/72

FOREIGN PATENT DOCUMENTS

| EP | 1 070 457 | 1/2001 |
| WO | WO 02/067698 | 9/2002 |
| WO | WO 03/028026 | 10/2003 |
| WO | WO 2007/065718 | 6/2007 |

OTHER PUBLICATIONS

Anderson et al. "Physicochemical Properties of Pronase-Treated Rice Glutelin" in JAOCS, vol. 78, No. 1 (2001) pp. 1-6.*

(Continued)

*Primary Examiner* — Elizabeth Gwartney
(74) *Attorney, Agent, or Firm* — Nixon & Vanderhye P.C.

(57) ABSTRACT

Partially deamidated rice endosperm protein or rice endosperm protein which is partially conjugated with mono-, di-, oligo- or polysaccharides is used as novel protective hydrocolloid for fat-soluble active ingredients and/or fat-soluble colorants. The present invention further includes compositions comprising that rice endosperm protein and at least one fat-soluble active ingredient/colorant, as well as their manufacture, that rice endosperm protein itself and its manufacture. These compositions are used for the enrichment, fortification and/or coloration of food, beverages, animal feed, personal care or pharmaceutical compositions. The present invention is directed to theses uses and to food, beverages, animal feed, personal care and pharmaceutical compositions containing such a rice endosperm protein and such a composition, respectively.

31 Claims, 1 Drawing Sheet

(56) References Cited

OTHER PUBLICATIONS

Kato et al. "Deamidation of Food Proteins by Protease in Alkaline pH" J. Agric. Food Chem. 1987 (35), pp. 224-227.*
Roche. Technical Specification Sheet, "Pronase", pp. 1-2, (2010).*
Shih et al. "Use of enzymes in the processing of protein products from rice bran and rice flour" Nahrung 43(a), 1999, pp. 14-18.*
International Search Report for PCT/EP2008/002315 mailed Jul. 21, 2008.
Ju et al., "Extraction, Denaturation and Hydrophobic Properties of Rice Flour Proteins", *Journal of Food Science*, vol. 66, No. 2, Mar. 1, 2001, pp. 229-232, XP009080240.
Prakash et al., "Effect of Stabilisation Treatment of Rice Bran on Functional Properties of Protein Concentrates", *Journal of the Science of Food and Agriculture*, vol. 67, No. 2, Feb. 1, 1995, pp. 181-187, XP000482338.

* cited by examiner

PROTECTIVE HYDROCOLLOID FOR ACTIVE INGREDIENTS

This application is the U.S. national phase of International Application No. PCT/EP2008/002315 filed 22 Mar. 2008 which designated the U.S. and claims priority to U.S. application Ser. No. 11/729,981 filed 30 Mar. 2007, the entire contents of each of which are hereby incorporated by reference.

The present invention is directed to the use of rice endosperm protein as novel protective hydrocolloid for fat-soluble active ingredients and/or fat-soluble colorants, whereby the rice endosperm protein is partially conjugated with mono-, di-, oligo- or polysaccharides (especially with mono- or polysaccharides) or partially deamidated. Moreover, the present invention is directed to compositions comprising that partially conjugated or partially deamidated rice endosperm protein and at least one fat-soluble active ingredient and/or fat-soluble colorant and to their manufacture, as well as to that partially conjugated or partially deamidated rice endosperm protein itself and its manufacture. The present invention is further directed to the use of such compositions for the enrichment, fortification and/or coloration of food, beverages, animal feed, personal care or pharmaceutical compositions, and to food, beverages, animal feed, personal care and pharmaceutical compositions containing such a partially conjugated or partially deamidated rice endosperm protein and such a composition, respectively.

Active ingredients, especially fat-soluble active ingredients or fat-soluble colorants, are often not added as such to food, beverages, animal feed, personal care and pharmaceutical compositions, but in form of formulations of the active ingredient in a hydroprotective colloid for reasons of enhancing properties such as chemical stability, (water-)solubility, free-flowing and controlled release etc. Known hydroprotective colloids are e.g. gelatine of different origin (poultry, bovine, pork, fish) and starch. Since hydroprotective colloids of animal origin are often not desired for religious or allergenic reasons and starch-based hydroprotective colloids might have low preference for consumers who are interested in gluten and corn-free products there is an on-going need for alternative hydroprotective colloids.

Rice endosperm proteins are recognized as nutritional and hypoallergenic and can, thus, be a suitable alternative source of protective hydrocolloid for formulations of active ingredients. However, high insolubility and poor functionality of rice endosperm protein at neutral pH limits its industrial application as a functional ingredient in food and pharmaceuticals products. The present invention overcomes these limitations and incorporates the rice endosperm protein which is partially conjugated with mono-, di-, oligo- or polysaccharides (especially with mono- or polysaccharides) or partially deamidated as a protective hydrocolloid for formulations of fat-soluble active ingredients and/or fat-soluble colorants.

Rice proteins rank high in nutritional quality in comparison to other cereals including corn and wheat, and are therefore perceived to have immense potential uses as food ingredients. Cereal grain proteins are rich in the essential amino acids cysteine and methionine. Lysine is the primary limiting amino acid in cereal proteins, but rice contains more lysine (3.8 g/16 g N) than other cereal proteins (wheat 2.3, corn 2.5 g/16 g N) (see reference 4 cited below). Although rice is generally regarded as having the lowest protein content (7.3%) among the common grains (wheat 10.6%, corn 9.8%, barley 11.0%, millet 11.5%), the net protein utilization of rice protein (73.8%) is the highest among the cereal grains (wheat 53.0%, corn 58.0%, barley 62.0%, millet 56.0%).

Compared with other cereal proteins, isolation of rice protein is difficult and therefore costly. The predominant rice protein, glutelin, is hydrophobic and is cross-linked with di-sulfide bonds. The extracted proteins are highly insoluble in nature and the conditions used in protein isolation further decrease their solubility, and thus have limited application as a functional ingredient. High-protein rice products can be obtained from rice flour by alkali extraction followed by precipitation at the isoelectric pH of the protein. Starch-hydrolyzing enzymes such as alpha-amylase, glucoamylase, and pullulanase are often used to separate proteins in rice flour by solubilizing and removing starch. In addition to starch hydrolyzing enzymes, cellulase and hemicellulase enzymes have been used to further increase the protein content in rice protein concentrate. However, information on suitable extraction methods and functionalities of such isolates is limited. Efficient extraction methods using approved food grade enzymes and chemicals are essential for commercial production and application of rice protein.

This need is fulfilled by the compositions of the present invention which comprise a rice endosperm protein which is partially conjugated with mono-, di-, oligo- or polysaccharides (especially with mono- or polysaccharides) or partially deamidated and a fat-soluble active ingredient and/or fat-soluble colorant.

BACKGROUND INFORMATION

1. Approved Methods of the American Association of Cereal Chemists, 8th Ed. AACC methods 1990, 44-16 and 46-12. The Association: St. Paul, Minn.
2. Achouri, A., Joyce Irene Boye, J. I., Yaylayan V. A., And Yeboah, F. K.: Functional Properties of Glycated Soy 11S Glycinin. J Food Sci. 2005, 70 (4), p. 269.
3. Baniel. A., Caer. D., Colas, B. and Gueguen, J.: Functional Properties of Glycosylated Derivatives of the 1 1s Storage Protein from Pea (*Pisum sativum* L.). J. Agric. Food Chem. 1992, 40, p. 200-205.
4. Bera M B, Mukherjee R K.: Solubility, emulsifying, and foaming properties of rice bran protein concentrates. J. Food Sci. 1989, 54(1), p. 142-145.
5. Cabra, V. Arreguin, R. Vazquez-Duhalt, R. Farres, A:. Effect of Alkaline Deamidation on the Structure, Surface Hydrophobicity, and Emulsifying Properties of the Z19 alpha-Zein J. Agric. Food Chem 2007, 55, p. 439-445.
6. Kato, A., Sasaki, Y., Furuta, R., and Kobayashi, K.: Functional protein polysaccharide conjugate prepared by controlled dry-heating of ovalbumin-dextran mixtures. Agric. Biol. Chem. 1990, 54, p. 107-112.
7. Kato, A., Shimokawa, K., and Kobayashi, K.: Improvement of the functional properties of insoluble gluten by Pronase digestion followed by dextran conjugation. J. Agric. Food Chem. 1991, 39, p. 1053-1056.
8. Kato, Y., Aoki, T., Kato, N., Nakamura, R., and Matsuda, T.: Modification of ovalbumin with glucose-6-phosphate by amino-carbonyl reaction. Improvement of protein heat stability and emulsifying activity. J. Agric. Food Chem. 1995, 43, p. 301-305.
9. Kinsella, J. E.: Functional properties of proteins in foods: a survey. Crit. Rev Food Sci. Nutr. 1976, 8(4), p. 19-80.
10. Nakamura S, Kato A, Kobayashi K.: Bifunctional lysozyme-galactomannan conjugate having excellent emulsifying properties and antibacterial effects. J Agric Food Chem 1992, 40, p. 735-9.
11. Nakamura, S., Saito, M., Goto, T., Saeki, H., Ogawa, M., Gotoh, G., Gohya, Y., and Hwang, J.-K.: Rapid formation of biologically active neoglycoprotein from lysozyme and 12. Nielsen, P. M., Petersen, D., and Dambmann, C.: Improved method for determining food protein degree of hydrolysis. J. Food Sci. 2001, 66 (5), 642-646.
13. Nielson, P. M.: Functionality of protein hydrolysates. In: Damodaran S, Paraf A, editors. Food proteins and their applications. 1st ed. New York: Marcel Dekker Inc. 1997, p. 443-72.
14. Oliver, C. M., Melton, L. D., & Stanley, R. A.: Creating proteins with novel functionality via the Maillard reaction: A review. Critical Reviews in Food Science and Nutrition 2006, 46, p. 337-350.
15. Paraman, I., Hettiarachchy, N. S., Schaefer, C., and Beck. M. I.: Hydrophobicity, Solubility, and Emulsifying Properties of Enzyme modified Rice Endosperm Protein. Submitted to Cereal chem. 2007, Manuscript ID. CC 10-06-0125
16. Pearce K N, Kinsella J E.: Emulsifying properties of proteins: evaluation of a turbidimetric technique. J Agric Food Chem 1978, 26, p. 716-722.
17. SAS (Statistical Analysis System). 2002. JMP® User's Guide, Version 5. SAS Institute Inc. Cary, N. C.
18. Schwenke K. D.: Enzyme and Chemical Modification of Proteins. Chapter 13 in "Food Proteins and their Applications" edited by A. Damodaran and A Paraf, 1997, Marcel Dekker, Inc., New York, USA.
19. Wen, T. N., and Luthe, D. S.: Biochemical characterization of rice glutelin. Plant Physiol. 1985, 78, p. 172-177.

DETAILED DESCRIPTION OF THE INVENTION

Compositions of the Present Invention

The compositions of the present invention may be solid compositions, i.e. stable, water-soluble or water-dispersible powders, or they may be liquid compositions, i.e. aqueous colloidal solutions or oil-in-water dispersions of the aforementioned powders. The stabilised oil-in-water dispersions, which may be oil-in-water emulsions or may feature a mixture of suspended, i.e. solid, particles and emulsified, i.e. liquid, droplets, may be prepared by the methods described below or by an analogous manner.

More specifically, the present invention is concerned with stable compositions in powder form comprising one or more fat-soluble active ingredient(s) and/or one or more fat-soluble colorant(s) in a matrix of a rice endosperm protein which is partially conjugated with mono-, di-, oligo- or polysaccharides (especially with mono- or polysaccharides) or partially deamidated.

Preferably the amount of that rice endosperm protein which is partially conjugated with mono-, di-, oligo- or polysaccharides (especially with mono- or polysaccharides) or partially deamidated is from 1 to 70 weight-%, more preferably from 5 to 50 weight-%, even more preferably from 10 to 40 weight-%, most preferably from 10 to 20 weight-% (with 20 weight-% being the most preferred one) and/or the amount of the fat-soluble active ingredient and/or fat-soluble colorant is from 0.1 to 90 weight-%, preferably from 1 to 80 weight-%, more preferably from 1 to 20 weight-%, based on the total amount of the composition. If additional adjuvants and/or excipients such as tocopherol and/or ascorbyl palmitate are present, they are present in an amount of from 0.01 to 50 weight-%, preferably in an amount of from 0.1 to 30 weight-%, more preferably from an amount of from 0.5 to 10 weight-%, based on the total amount of the composition.

Rice Endosperm Protein which is Partially Conjugated with Mono-, Di-, Oligo- or Polysaccharides (Especially with Mono- or Polysaccharides) or Partially Deamidated In preferred embodiments of the present invention the rice endosperm protein is a modified rice endosperm protein whose manufacture is described below.

An especially preferred rice protein is one obtained by the following steps: alkaline extraction, (enzymatically modification, especially with Alkalase), partial cross-linking with at least one compound selected from the group consisting of mono-, di-, oligo- and polysaccharides (especially from the group consisting of mono- and polysaccharides), centrifugation and ultra-filtration. A further especially preferred rice protein is one obtained by the following steps: alkaline extraction, (enzymatically modification, especially with Alkalase), partial deamidation, centrifugation and ultra-filtration.

If needed for the further use the thus obtained modified rice endosperm protein may also be dried.

In preferred embodiments of the invention the used rice endosperm proteins which are partially conjugated with mono-, di-, oligo- or polysaccharides (especially with mono- or polysaccharides) or partially deamidated have an emulsion activity of ≥0.2, preferably of ≥0.45, more preferably of ≥0.5, even more preferably of from 0.5 to 1.0. The determination of the emulsion activity is described in example 1. The present invention refers also to these rice endosperm proteins which are partially conjugated with mono-, di-, oligo- or polysaccharides (especially with mono- or polysaccharides) or partially deamidated themselves.

The amount of the rice endosperm protein which is partially conjugated with mono-, di-, oligo- or polysaccharides (especially with mono- or polysaccharides) or partially deamidated may be in the range of from 1 to 70 weight-%, preferably in the range of from 5 to 50 weight-%, more preferably in the range of from 10 to 40 weight-%, most preferably in the range of from 10 to 20 weight-%, based on the total weight of the composition as disclosed below.

Fat-Soluble Active Ingredient and/or Fat-Soluble Colorant

The fat-soluble active ingredients are preferably those ingredients with a pharmacological effect or those providing health benefits to the human or animal body in general. "Fat-soluble" (fat-soluble active ingredient/fat-soluble colorant) in the context of the present invention means that the compound is hardly soluble in water at room temperature and at atmospheric pressure.

The fat-soluble active ingredient and/or the fat-soluble colorant is preferably selected from the group consisting of carotenes and structurally related polyene compounds, fat-soluble vitamins, coenzyme Q10, polyunsaturated fatty acids such as eicosapentaenoic acid (EPA) and docosahexaenoic acid (DHA) and esters thereof (such as the ethyl esters or the triglycerides (containing the same or different fatty acids)), mono-, di-, triglycerides rich in polyunsaturated fatty acids, fat-soluble UV-A filters, UV-B filters, as well as their physiologically acceptable derivatives such as their esters, especially with $C_{1-20}$ carbonic acids, and any mixtures of them.

The most preferred fat-soluble vitamins are Vitamin A or E.

Preferred examples of the carotenes and structurally related polyene compounds are carotenoids such as α-carotene, β-carotene, 8'-apo-β-carotenal, 8'-apo-β-carotenoic acid esters such as the ethyl ester, canthaxanthin, astaxanthin, lycopene, lutein, zeaxanthin, crocetin, α-zeacarotene, β-zeacarotene, as well as their physiologically acceptable derivatives such as their esters, especially with $C_{1-20}$ carbonic acids, and any mixtures of them.

The most preferred carotenoid is β-carotene.

The term "β-carotene" encompasses the all-cis as well as the all-trans isomers and all possible mixed cis-trans-isomers. The same applies for the other carotenoids.

The term "zeaxanthin" encompasses the natural R,R-zeaxanthin, as well as S,S-zeaxanthin, meso-zeaxanthin and any mixture of them. The same applies for lutein.

The fat-soluble active ingredients may be of natural origin, i.e. isolated/extracted from plants, purified and/or concentrated, as well as those synthesized by chemical and/or microbiological (fermentative) routes.

The amount of the fat-soluble active ingredient and/or the fat-soluble colorant may be in the range of from 0.1 to 90 weight-%, preferably in the range of from 1 to 80 weight-%, more preferably in the range of from 1 to 20 weight-%, based on the total weight of the composition as disclosed below.

Further Components

Beside the active ingredient and the rice endosperm protein which is partially conjugated with mono-, di-, oligo- or polysaccharides (especially with mono- or polysaccharides) or partially deamidated the compositions of the present invention may preferably additionally contain at least one water-soluble antioxidant and/or fat-soluble antioxidant. The amount of the water-soluble antioxidant and/or fat-soluble antioxidant may be in the range of from 0.1 to 10.0 weight-%, preferably in the range of from 0.5 to 5.0 weight-%, more preferably in the range of from 0.5 to 3.0 weight-%, based on the total weight of the composition.

The water-soluble antioxidant may be for example ascorbic acid or a salt thereof, preferably sodium ascorbate, water-soluble polyphenols such as hydroxytyrosol and oleuropein aglycon; epigallocatechingallate (EGCG) or extracts of rosemary or olives.

The fat-soluble antioxidant may be for example a tocopherol, e.g. dl-α-tocopherol (i.e. synthetic tocopherol), d-α-tocopherol (i.e. natural tocopherol), β- or γ-tocopherol, or a mixture of two or more of these; butylated hydroxytoluene (BHT); butylated hydroxyanisole (BHA); ethoxyquin, propyl gallate; tert. butyl hydroxyquinoline; or 6-ethoxy-1,2-di hydroxy-2,2,4-trimethylquinoline (EMQ), or an ascorbic acid ester of a fatty acid, preferably ascorbyl palmitate or stearate.

The compositions of the present invention may further contain a co-emulgator selected from the group consisting of mono- and diglycerides of fatty acids, polyglycerol esters of fatty acids, lecithins; N-acylated amino acids and derivatives thereof, N-acylated peptides with an alkyl or alkenyl radical, and salts thereof; alkyl or alkenyl ether or ester sulfates, and derivatives and salts thereof; polyoxyethylenated alkyl or alkenyl fatty ethers or esters; polyoxyethylenated alkyl or alkenyl carboxylic acids and salts thereof; N-alkyl or N-alkenyl betaines; alkyltrimethylammonium or alkenyltrimethylammonium and salts thereof; polyol alkyl or alkenyl ether or ester; and mixtures thereof.

Preferred examples of polyol alkyl or alkenyl ethers or esters are sorbitan alkyl or alkenyl esters polyoxyethylenated with at least 20 units of ethylene oxide, such as sorbitan palmitate 20 EO or Polysorbate 40 marketed under the tradename Montanox 40 DF by the company Seppic, sorbitan laurate 20 EO or Polysorbate 20 marketed under the tradename Tween 20 by the company ICI, and sorbitan monostearate.

The amount of the co-emulgator may be in the range of from 0 to 90 weight-%, preferably in the range of from 0 to 50 weight-%, more preferably in the range of from 0 to 20 weight-%, based on the total weight of the composition.

The formulations according to the present invention may further be pressed into tablets, whereby one or more excipients and/or adjuvants selected from the group consisting of monosaccharides, disaccharides, oligosaccharides and polysaccharides, glycerol, and triglycerides, may be added.

Preferred examples of mono- and disaccharides which may be present in the compositions of the present invention are sucrose, invert sugar, xylose, glucose, fructose, lactose, maltose, saccharose and sugar alcohols.

Preferred examples of the oligo- and polysaccharides are starch, modified starch and starch hydrolysates. Preferred examples of starch hydrolysates are dextrins and maltodextrins, especially those having the range of 5 to 65 dextrose equivalents (DE), and glucose syrup, especially such having the range of 20 to 95 DE. The term "dextrose equivalent" (DE) denotes the degree of hydrolysis and is a measure of the amount of reducing sugar calculated as D-glucose based on dry weight; the scale is based on native starch having a DE close to 0 and glucose having a DE of 100.

The triglyceride is suitably a vegetable oil or fat, preferably corn oil, sunflower oil, soybean oil, safflower oil, rapeseed oil, peanut oil, palm oil, palm kernel oil, cotton seed oil, olive oil or coconut oil.

The amount of the excipient(s) and/or adjuvant(s) may be in the range of from 0.1 to 50 weight-%, preferably in the range of from 0.1 to 30 weight-%, more preferably in the range of from 0.5 to 10 weight-%, based on the total weight of the composition.

Solid compositions may in addition contain an anti-caking agent, such as silicic acid or tricalcium phosphate and the like, and up to 10 weight-%, as a rule 2 to 5 weight-%, of water.

The amount of the anti-caking agent may be in the range of from 0 to 5 weight-%, preferably in the range of from 0 to 3 weight-%, more preferably in the range of from 0.2 to 3.0 weight-%, based on the total weight of the composition.

Manufacture of the Composition

An object of the present invention is also a process for the manufacture of the composition of the present invention which comprises the following steps:

I) preparing an aqueous solution or colloidal solution of a rice endosperm protein which is partially conjugated with mono-, di-, oligo- or polysaccharides (especially with mono- or polysaccharides) or partially deamidated, (manufacture of such a rice endosperm protein is described below), II) optionally adding at least a water-soluble excipient and/or adjuvant to the solution prepared in step I), III) preparing a solution or dispersion of at least a fat-soluble active ingredient and/or fat-soluble colorant, and optionally at least a fat-soluble adjuvant and/or excipient, IV) mixing the solutions prepared in step I) to III) with each other, V) homogenising the thus resulting mixture, VI) optionally adding a cross-linking agent for partially cross-linking said rice endosperm protein which is partially conjugated with mono-, di-, oligo- or polysaccharides (especially with mono- or polysaccharides) or partially deamidated, VIa) optionally submitting the mixture resulting after having performed step VI) to enzymatic treatment or heat treatment to partially cross-link the rice endosperm protein which is partially conjugated with mono-, di-, oligo- or polysaccharides (especially with mono- or polysaccharides) or partially deamidated;

VII) optionally converting the dispersion obtained in step V) and/or VI) into a powder, VIII) optionally drying the powder obtained in step VII), IX) optionally submitting the dry powder to heat treatment or to enzymatic treatment to cross-link the (modified) rice endosperm protein,
with the proviso that only step VIa) or step IX) is carried out, but not both, when step VI) is carried out.

Step I

This step is simply performed by adding water to the rice endosperm protein which is partially conjugated with mono-, di-, oligo- or polysaccharides (especially with mono- or polysaccharides) or partially deamidated (manufacture see below) or vice versa, optionally under stirring. Alternatively homogenization may be possible via ultrasonication.

Preferably the rice endosperm protein which is partially conjugated with mono-, di-, oligo- or polysaccharides (especially with mono- or polysaccharides) or partially deamidated is used with the preferences as described above and below.

Step II

Water-soluble excipients and/or adjuvants that may be added are e.g. monosaccharides, disaccharides, oligosaccharides and polysaccharides, glycerol and water-soluble antioxidants. Examples of them are given above.

Step III

Fat-soluble active ingredients and fat-soluble colorants are those as described above.

The (fat-soluble) active ingredient and/or fat-soluble colorant and optional fat-soluble excipients and adjuvants are either used as such or dissolved or suspended in a triglyceride and/or an (organic) solvent.

Suitable organic solvents are halogenated aliphatic hydrocarbons, aliphatic ethers, aliphatic and cyclic carbonates, aliphatic esters and cyclic esters (lactones), aliphatic and cyclic ketones, aliphatic alcohols and mixtures thereof.

Examples of halogenated aliphatic hydrocarbons are mono- or polyhalogenated linear, branched or cyclic C1- to C15-alkanes. Especially preferred examples are mono- or polychlorinated or -brominated linear, branched or cyclic C1- to C15-alkanes. More preferred are mono- or polychlorinated linear, branched or cyclic C1- to C15-alkanes. Most preferred are methylene chloride and chloroform.

Examples of aliphatic esters and cyclic esters (lactones) are ethyl acetate, isopropyl acetate and n-butyl acetate; and γ-butyrolactone.

Examples of aliphatic and cyclic ketones are acetone, diethyl ketone and isobutyl methyl ketone; and cyclopentanone and isophorone.

Examples of cyclic carbonates are especially ethylene carbonate and propylene carbonate and mixtures thereof.

Examples of aliphatic ethers are dialkyl ethers, where the alkyl moiety has 1 to 4 carbon atoms. One preferred example is dimethyl ether.

Examples of aliphatic alcohols are ethanol, iso-propanol, propanol and butanol.

Furthermore any oil (triglycerides), orange oil, limonen or the like and water can be used as a solvent.

Fat-soluble excipients and/or adjuvants that may be added are e.g. corn oil, mono- or diglycerides of fatty acids, polyglycerol fatty acids, and middle chain triglycerides ("MCT").

Step IV

In an alternative process of the present invention step III) is not carried out, but the fat-soluble active ingredient and/or fat-soluble colorant and the optional fat-soluble excipient and/or adjuvant is directly added to the solution of step I) or II).

Step V

For the homogenisation conventional technologies, such as high-pressure homogenisation, high shear emulsification (rotor-stator systems), micronisation, wet milling, microchanel emulsification, membrane emulsification or ultrasonification can be applied. Other techniques used for the preparation of compositions containing fat-soluble active ingredient(s) and/or fat-soluble colorant(s) for enrichment fortification and/or coloration of food, beverages, animal feed, cosmetics or pharmaceutical compositions are disclosed in EP-A 0 937 412 (especially paragraphs [0008], [0014], [0015], [0022] to [0028]), EP-A 1 008 380 (especially paragraphs [0005], [0007], [0008], [0012], [0022], [0023] to [0039]) and in U.S. Pat. No. 6,093,348 (especially column 2, line 24 to column 3, line 32; column 3, line 48 to 65; column 4, line 53 to column 6, line 60), the contents of which are incorporated herein by reference.

Step VI

The cross-linking agent is preferably selected from the group consisting of reducing sugars, glycoproteins, and glycopeptides. Thus an intermolecular cross-linking between the (modified) rice endosperm protein and the sugar or sugar part of the glycoprotein/glycopeptide is formed. Preferred examples of the cross-linking agent are the monosaccharides (fructose glucose, galactose, xylose), disaccharides (saccharose, lactose), oligosaccharides (dextrin) and polysaccharides (Xanthan gum, pectin), most preferred are fructose, glucose and Xanthan gum.

Glycoprotein is a compound containing carbohydrate (or glycan) covalently linked to protein. The carbohydrate may be in the form of a monosaccharide, disaccharide, oligosaccharide, polysaccharide, or their derivatives (e.g. sulfo- or phospho-substituted).

Preferred examples of glycoproteins are egg albumin, milk casein.

A glycopeptide is a compound consisting of carbohydrate linked to an oligopeptide composed of L- and/or D-amino acids. A glyco-amino-acid is a saccharide attached to a single amino acid by any kind of covalent bond.

A preferred example of glycopeptides is milk lactoferrin, an iron-binding glycopeptide.

Thus, in contrast to co-pending PCT/EP2006/011873 here the rice endosperm protein which is partially conjugated with mono-, di-, oligo- or polysaccharides (especially with mono- or polysaccharides) or partially deamidated may further be partially cross-linked with at least one compound selected from the group consisting of reducing sugars, glycoproteins or glycopeptides.

Step VIa

The cross-linking can be achieved by submitting mixtures additionally containing a cross-linking agent as described above to heat-treatment to cause cross-linking of the sugar with the protein in a Maillard type reaction, i.e. by thermally treatment, preferably at temperatures from about 30 to about 160° C., more preferably at temperatures from about 70 to about 100° C., most preferably at temperatures from about 80 to about 90° C.

Cross linking is an enzymatic or a non-enzymatic reaction resulting from the initial condensation between an available amino group of protein and a carbonyl-group of mono-, di-, oligo- or polysaccharides (especially of mono- or polysaccharides). Cross linking is a specific type of modification which is being used to alter protein physicochemical and functional performance such as improving emulsification, encapsulation.

Further partial cross-linking of the rice endosperm protein which is partially conjugated with mono-, di-, oligo- or polysaccharides (especially with mono- or polysaccharides) or partially deamidated with the cross-linking agent can also be achieved by treatment with cross-linking enzymes (acyltransferases, EC 2.3, e.g. transglutaminase, EC 2.3.2.13, protein-glutamine:γ-glutamyltransferase), i.e. by enzymatically treatment, conveniently carried out at temperatures from about 0 to about 70° C., preferably at temperatures from about 20 to about 40° C. Preferably the enzymatic treatment according to step VIa) is a treatment with a cross-linking enzyme, particularly with a transglutaminase.

Enzymatic cross-linking results in stable protein-containing polysaccharide networks, in the case of a transglutaminase by the formation of ε-(γ-glutamyl)-lysine isopeptide bonds. The use of glycoproteins or glycopeptides is preferred for the enzymatic cross-linking.

Both techniques, heat-treatment to cause cross-linking of the sugar with the protein in a Maillard type reaction and enzymatic cross-linking can be used for the incorporation of lipophilic moieties and can be carried out either in a dried form of the composition (step IX), or in an aqueous solution or suspension (step VIa). The enzymatic cross-linking is preferably carried out in an aqueous solution or suspension.

Step VII

The so-obtained dispersion, which is an oil-in-water dispersion, can be converted after removal of the organic solvent (if present) into a solid composition, e.g. a dry powder, using any conventional technology such as spray drying, spray drying in combination with fluidised bed granulation (the latter technique commonly known as fluidised spray drying or FSD), or by a powder-catch technique whereby sprayed emulsion droplets are caught in a bed of an absorbent, such as starch, calcium silicate and silicon dioxide, and subsequently dried.

Spray-drying may be performed at an inlet-temperature of from about 100 to about 250° C., preferably of from about 150° C. to about 200° C., more preferably of from about 160 to about 190° C., and/or at an outlet-temperature (product temperature) of from about 45 to about 160° C., preferably of from about 55 to about 110° C., more preferably of from about 65 to about 95° C.

Step VIII

The drying of the powder obtained in step VII is preferably carried out at a temperature of ≤100° C., preferably at a temperature of from 20 to 100° C., more preferably at a temperature of from 60 to 70° C. If the drying is performed in vacuum the temperature is lower.

Step IX

The cross-linking via heat-treatment is carried out as already described above for step VIa. The same applies for the enzymatic treatment, which is, however, preferably carried out in solution/suspension.

Manufacture of the Rice Endosperm Protein which is Partially Conjugated with Mono-, Di-, Oligo- or Polysaccharides (Especially with Mono- or Polysaccharides) or Partially Deamidated The present invention is also directed to a process for the manufacture of a rice endosperm protein which is partially conjugated with mono-, di-, oligo- or polysaccharides (especially with mono- or polysaccharides) or partially deamidated starting from milled rice, whereby the rice bran was removed before milling, comprising the following steps a) to e):

a) preparing an aqueous solution or suspension of milled rice, whereby the rice bran was removed before milling, whereby the solution or suspension preferably has a dry mass content of from 0.1 to 30 weight-%, preferably from 10 to 15 weight-%, based on the total amount of the aqueous solution or suspension;

b) removing the non-protein part or the protein part of the milled rice, whereby the rice bran was removed before milling, to obtain the rice endosperm protein;

c) modifying the protein part of the milled rice, whereby the rice bran was removed before milling, by reacting the protein part of the milled rice partially with mono-, di-, oligo- or polysaccharides (especially with mono- or polysaccharides) in a Maillard-type reaction or by partially deamidating the protein part of the milled rice to obtain rice endosperm protein which is partially conjugated with mono-, di-, oligo- or polysaccharides (especially with mono- or polysaccharides) or partially deamidated;

d) optionally isolating the rice endosperm protein which is partially conjugated with mono, di-, oligo- or polysaccharides (especially with mono- or polysaccharides) or partially deamidated;

e) optionally converting the rice endosperm protein which is partially conjugated with mono-, di-, oligo- or polysaccharides (especially with mono- or polysaccharides) or partially deamidated into a solid form.

Step a)

Milled rice, where the rice bran was removed before milling, is also known under the expression "rice flour".

This step is simply performed by adding water to the rice flour or vice versa, optionally by stirring vigorously (with a mechanical stirrer) until the rice flour is completely dispersed, or by homogenizing the rice flour suspension with a homogenizer, e.g. for 5 minutes at room temperature.

Step b)

Step b) may be performed as described by Paraman, I., Hettiarachchy, N. S., Schaefer, C., and Beck. M. I. in Cereal Chem. 2006, 83(6), 663-667: "Physicochemical properties of rice endosperm proteins extracted by chemical and enzymatic methods".

Removing of the Non Protein Part

Step b) may preferably be achieved by treating the rice flour with non-protein degrading enzymes, e.g. with a 0.5% aqueous suspension of Termamyl® at a temperature of 90° C. for 2 hours and then with a 0.1% aqueous suspension of a cellulase at a temperature of 50° C. for 30 minutes—without any pH adjustment (pH 6-7), deactivating the enzymes, separating and removing the non-protein part from the protein part of the rice flour.

Preferred examples of non-protein degrading enzymes are starch-degrading enzymes such as α-amylases and cellulases, i.e. cellulose-degrading enzymes, and mixtures thereof. A preferred example of an α-amylase is Termamyl® 120, Type L, commercially available from Novo Nordisk Biochem, North America, Inc., USA. Other preferred examples are Liquzyme® Supra, commercially available from Novo Nordisk Biochem, North America, Inc., USA, Amylase S "Amano" 35 G, commercially available from Amano Pharmaceutical Co. Ltd., Nagoya, Japan, Multifect Cellulase, commercially available from Genencor International, Inc., USA, and Cellulase T "Amano" 4, commercially available from Amano Pharmaceutical Co. Ltd., Nagoya, Japan.

The reaction of the enzymes can be stopped by neutralising the solution or suspension if an inorganic acid (e.g. hydrochloric acid) or an organic acid (e.g. citric acid) or base is used or by heating to denature the enzymes.

The denaturation may be achieved by heating the solution to a temperature of from 80 to 95° C., preferably to a temperature of from 80 to 85° C. (especially at a low pH of from 3.5 to 4.5) for 10 to 15 minutes. Afterwards the solution may be cooled to 50° C.

The separation of the non-protein part may be achieved by centrifugation (5000 g for 15 minutes) (whereby the non-protein part is in the water phase), followed by washing with deionized water. The rice endosperm protein remains in pellets.

Removing of the Protein Part

Alternatively a so-called "alkaline extraction" or a so-called "salt-extraction" may be performed before the centrifugation or filtration.

"Alkaline extraction" means that first the pH of the solution or suspension of the rice flour is adjusted to a value of from 7 to 12, preferably to a value of from 8 to 10, more preferably to a value of about 9, with an alkali solution (e.g. an aqueous NaOH solution) at 40 to 60° C. for 3 hours.

In cases where the protein yield is more important than the protein functionality it may be advantageous to adjust the pH preferably to a value of from 8 to 12, more preferably of from 9 to 12, even more preferably from 10 to 12.

Preferably such a base has a concentration of about 0.1 to 5 M, preferably of about 0.5 to about 2 M. The base may be an inorganic base. Examples of inorganic bases are (earth) alkali hydroxides such as sodium hydroxide (preferred), potassium hydroxide and calcium hydroxide.

A "salt-extraction" is similar to an "alkali-extraction", but in addition to the base a salt such as sodium chloride is used. In a preferred embodiment of the invention an aqueous 0.08 M sodium chloride solution (adjusted to pH 11 with NaOH) is used as the extracting solvent.

In both cases (alkaline or salt extraction) the protein part is transferred to the water phase. The protein part may be separated then by centrifugation or filtration from the non-protein part.

Further Modification of the Protein Part

A further modification of the rice flour may be achieved by treating it(s protein part) with (commercially available) food grade alkaline, neutral and/or acid proteases. For some proteases the enzyme specifications and the optimum conditions are given in the tables below.

TABLE 1a

Enzyme specification I

| Enzyme | Type of protease | Source | Preferential specificity |
|---|---|---|---|
| Protex 6L | Serine Protease | *Bacillus licheniformis* | Hydrolysis of proteins with broad specificity for peptide bonds |
| Bromelain | Cysteine Protease | Pineapple stem | Broad specificity, but strong preference for Arg-Arg in peptides |
| Alkalase | Serine Protease | *Bacillus licheniformis* | Broad specificity, and a preference for a large uncharged residue's carboxyl sites |
| Liquipanol | Cysteine Protease | Concentrated papain | Broad specificity |
| Alkaline protease | Serine Protease | Bacterial protease | Hydrolysis of proteins with broad specificity for peptide bonds |
| Pepsin | Aspartic Protease | Porcine stomach | The C-terminal side of tyrosine, phenylalanine, and tryptophan residues |

TABLE 1b

Enzyme specification II

| Enzymes | pH-range | Activity/g | Company |
|---|---|---|---|
| Protex 6L | 6-10 | 580 000 | Genencor International, Inc., Rochester, NY 14618, USA |
| Bromelain | 5-8 | 150 000 | Enzyme Development Corporation, New York, NY 10001, USA. |
| Alkalase | 6-9 | 2.4 AU | Novo Nordisk Biochem, Franklinton, NC 27525, USA |
| Liquipanol | 5-8 | 125 000 | Enzyme Development Corporation, New York, NY 10001, USA. |

TABLE 1b-continued

Enzyme specification II

| Enzymes | pH-range | Activity/g | Company |
|---|---|---|---|
| Alkaline protease | 6-9 | 175 000 | Enzyme Development Corporation, New York, NY 10001, USA. |

TABLE 2

The optimum enzyme conditions used in protein hydrolysis

| Enzyme | Amount of Enzyme [weight-%, based on protein weight] | pH | Temperature [° C.] | Time [minutes] |
|---|---|---|---|---|
| Liquipanol | 1.0 | 8.0 | 50 | 60 |
| Bromelain | 1.0 | 7.0 | 50 | 60 |
| Alkalase | 1.0 | 9.0 | 60 | 60 |
| Protex 6L | 1.0 | 10.0 | 60 | 60 |
| Pepsin | 0.5 | 3.0 | 37 | 30 |

The proteases may be from bacteria or fungi, as well as from fruit or may have animal origin.

Examples of alkaline proteases are the commercially available Alkalase® (Novo Nordisk Biochem, Franklinton, N.C., USA), Alkaline Protease® (Enzyme Development Corporation, New York, N.Y., USA), Protex 6L® (Genencor® Bacterial Alkaline Protease, Genencor International, Inc., Rochester, N.Y., USA) and Genencor® Protease 899 (Genencor International, Inc., Rochester, N.Y., USA).

Examples of neutral proteases are the commercially available Bromelain® (Enzyme Development Corporation, New York, N.Y., USA), Liquipanol® (Enzyme Development Corporation, New York, N.Y., USA) and bacterial neutral-protease (Genencor International, Inc., Rochester, N.Y., USA). A further example of a neutral protease is the commercially available Collupilin® of DSM Food Beverages, Delft, Netherlands, produced from *Carica papaya*, a plant, i.e. an enzyme of fruit origin.

Examples of acid proteases are pepsin (Sigma, USA) and Acid protease (Amano Pharmaceutical Co. Ltd., Nagoya, Japan).

In a preferred embodiment of the process of the present invention the protein part of the rice flour is treated subsequently by two different alkaline proteases at a pH range of from 7 to 10 for 10 to 80 minutes at 40 to 60° C.

Preferably one of these proteases is a serine specific protease such as Alkalase®, Protex 6L® or Alkaline Protease® and the other is a cysteine specific protease such as Liquipanol® or Bromelain®.

This modification step may also be modified by not adding the enzyme(s) at once but by adding them (subsequently or simultaneously) portion wise.

Step c)

The protein part obtained in step b) is used as starting material for performing step c), i.e. either a partial reaction with mono- (di- or oligo-) or polysaccharides or a partial deamidation.

Partial Reaction of the Protein Part of the Milled Rice with Mono-, Di-, Oligo- or Polysaccharides (Especially with Mono- or Polysaccharides)

The reaction of the protein part with the mono-, di-, oligo- or polysaccharides proceeds in a Maillard-type reaction. Aqueous dispersions of the protein part and aqueous solutions/dispersions of the mono-, di-, oligo- or polysaccharide (especially of the mono- or polysaccharide), respectively, may be prepared separately and then added together under stirring.

Usually the aqueous solution of the mono- or polysaccharide (or di- or oligosaccharide), most preferably having a concentration of 10 weight-%, was slowly added to the aqueous solution of the protein part, most preferably having a concentration of 10 weight-%, under stirring to obtain a mixture of both solutions/dispersions. The mixing is preferably carried out at a temperature in the range of from 20 to 60° C., preferably in the range of from 30 to 50° C., more preferably in the range of from 35 to 45° C., and for a time in the range of from 10 minutes to 2 hours, preferably in the range of from 30 minutes to 90 minutes, more preferably in the range of from 45 minutes to 60 minutes.

Then the pH value of the mixture is adjusted to a value in the range of from 6.0 to 9.0, preferably to a value in the range of from 6.5 to 8.5, preferably to a value in the range of from 7.0 to 8.0 by adding a base, preferably in form of an aqueous solution. Preferably such a base has a concentration of about 0.1 to 3 M, preferably of about 0.5 to about 2 M.

The base may be an inorganic base. Examples of inorganic bases are (earth) alkali hydroxides such as sodium hydroxide (most preferred), potassium hydroxide (preferred) and calcium hydroxide.

The thus obtained alkaline mixture is then dried, preferably by spray-drying. The spray-drying is preferably carried out at an inlet-temperature in the range of from 50° C. to 250° C., more preferably in the range of from 60° C. to 100° C., most preferably in the range of from 60 to 90° C.

The reaction (cross-linking) may then be performed by incubating the dried protein and mono- or polysaccharide (or di- or oligosaccharide) mixture to a temperature in the range of from 30 to 70° C., preferably in the range of from 40 to 60° C., more preferably in the range of from 45 to 55° C. in a humidity chamber. Depending on the reaction temperature the duration of the reaction is in a time range from 2 hours to 60 hours, preferably from 4 hours to 40 hours, more preferably from 6 hours to 30 hours. The relative humidity may vary in a range of from 39 to 85%, more preferably in the range of from 44 to 79%, most preferably in the range of from 54 to 69%, to maintain the water activity at a range of from 0.5 to 0.8.

The cross-linking may also be carried out by enzymatic treatment as already described above for step VIa.

Preferred examples of monosaccharides are pentoses and hexoses (fructose, glucose, galactose, xylose, especially fructose and glucose).

Preferred examples of polysaccharides are Xanthan gum and pectin.

Instead of mono- or polysaccharides also disaccharides (saccharose, lactose) and oligosaccharides (dextrin) may be used.

The weight ratio of the protein part to the monosaccharide lies in the range of from 0.5 to 12% (w/w), preferably in the range of from 0.1 to 8% (w,w), more preferably in the range of from 0.5 to 4% (w/w).

The weight ratio of the protein part to the polysaccharide (or disaccharide or oligosaccharide) lies in the range of from 0.1 to 20% (w,w), preferably in the range of from 0.5 to 20% (w/w).

If glucose is used as monosaccharide the weight ratio of glucose to the protein part obtained in step b) is preferably in the range of from 0.1 to 8% (w/w), more preferably in the range of from 0.5 to 4% (w/w).

If Xanthan gum is used as polysaccharide the weight ratio of Xanthan gum to the protein part obtained in step b) is preferably in the range of from 0.1 to 20% (w/w), more preferably in the range of from 0.5 to 10% (w/w).

Partial Deamidation of the Protein Part of the Milled Rice

The deamidation is performed by adjusting the pH value of an aqueous colloidal solution of the protein part of the rice endosperm protein obtained in step b) to a value in the range of from 9.0 to 13.0, preferably to a value in the range of from 9.5 to 12.5, preferably to a value in the range of from 10.5 to 12 by adding a base, preferably in form of an aqueous solution. Preferably such a base has a concentration of about 0.1 to 3 M, preferably of about 0.5 to about 2 M. The base may be an inorganic base. Examples of inorganic bases are (earth) alkali hydroxides such as sodium hydroxide (most preferred), potassium hydroxide (preferred) and calcium hydroxide.

The thus resulting alkaline mixture is then brought to a temperature in the range of from 25 to 90° C., preferably in the range of from 30 to 80° C., more preferably in the range of from 40 to 70° C.

Depending on the deamidation temperature the duration of the deamidation is in a time range from 0.5 hours to 24 hours, preferably from 0.5 to 12 hours, more preferably from 0.5 to 6 hours.

Step d)

Step d) may be performed by any method known to the person skilled in the art for isolating proteins.

Step d) may e.g. be carried out by centrifugation and/or filtration.

Usually it is not necessary to isolate the protein partially conjugated with mono-, di-, oligo- or polysaccharides or partially deamidated.

Step e)

The conversion into a solid form, e.g. a dry powder, can be achieved by any drying method known to the person skilled in the art. Preferred are spray drying or freeze-drying. Spray drying is preferably performed at an inlet temperature of 200° C. to 240° C. and at an outlet temperature of 80 to 100° C. The freeze-drying is preferably performed at a temperature of from about −20° C. to about −50° C. for 10 to 48 hours.

An object of the present invention is also the rice endosperm protein which is partially conjugated with mono-, di-, oligo- or polysaccharides (especially with mono- or polysaccharides) or partially deamidated itself, especially the one as obtainable by any process as described above. Even more preferred is the rice endosperm protein which is partially conjugated with mono-, di-, oligo- or polysaccharides (especially with mono- or polysaccharides) or partially deamidated itself as obtained by any process as described above.

INDUSTRIAL APPLICABILITY

The present invention is directed to the use of a composition as described above for the enrichment, fortification and/or coloration of food, beverages, animal feed, personal care or pharmaceutical compositions, as well as to the food, beverages, animal feed, personal care and pharmaceutical compositions containing such a composition as described above themselves.

The present invention is also directed to food, beverages, animal feed, personal care and pharmaceutical compositions containing a rice endosperm protein which is partially conjugated with mono-, di-, oligo- or polysaccharides (especially with mono- or polysaccharides) or partially deamidated as described above, as well as to the use of such a rice endosperm protein (with the preferences as described above) as protective hydrocolloid for fat-soluble active ingredients and/or fat-soluble colorants.

Animals including humans in the context of the present invention encompass besides humans especially farm animals such as sheep, cow, horses, poultry (broiler and egg pigmentation), shrimps and fish (especially salmon and rainbow trout) as well as pets such as cat, dogs, birds (e.g. flamingos) and fish.

Beverages wherein the compositions of the present invention can be used, especially as a colorant or a functional ingredient, can be carbonated beverages e.g., flavoured seltzer waters, soft drinks or mineral drinks, as well as non-carbonated beverages e.g. flavoured waters, fruit juices, fruit punches and concentrated forms of these beverages. They may be based on natural fruit or vegetable juices or on artificial flavours. Also included are alcoholic beverages and instant beverage powders. Besides, sugar containing beverages, diet beverages with non-caloric and artificial sweeteners are also included.

Further, dairy products, obtained from natural sources or synthetic, are within the scope of the food products wherein the compositions of the present invention can be used, especially as a colorant or as a functional ingredient. Typical examples of such products are milk drinks, ice cream, cheese, yoghurt and the like. Milk replacing products such as soymilk drinks and tofu products are also comprised within this range of application.

Also included are sweets which contain the compositions of the present invention as a colorant or as a functional ingredient, such as confectionery products, candies, gums, desserts, e.g. ice cream, jellies, puddings, instant pudding powders and the like.

Also included are cereals, snacks, cookies, pasta, soups and sauces, mayonnaise, salad dressings and the like which contain the compositions of the present invention as a colorant or a functional ingredient. Furthermore, fruit preparations used for dairy and cereals are also included.

The final concentration of the fat-soluble active ingredient and/or the fat-soluble colorant which is added via the compositions of the present invention to the food products may be from 0.1 to 500 ppm, particularly from 1 to 50 ppm, based on the total weight of the food composition and depending on the particular food product to be coloured or fortified and the intended grade of coloration or fortification.

The food compositions of this invention are preferably obtained by adding to a food product the fat-soluble active ingredient and/or the fat-soluble colorant in the form of a composition of this invention. For coloration or fortification of a food or a pharmaceutical product a composition of this invention can be used according to methods per se known for the application of water dispersible solid compositions of the present invention.

In general the composition may be added either as an aqueous stock solution, a dry powder mix or a pre-blend with other suitable food ingredients according to the specific application. Mixing can be done e.g. using a dry powder blender, a low shear mixer, a high-pressure homogeniser or a high shear mixer depending on the formulation of the final application. As will be readily apparent such technicalities are within the skill of the expert.

Pharmaceutical compositions such as tablets or capsules wherein the compositions are used as a colorant are also within the scope of the present invention. The coloration of tablets can be accomplished by adding the compositions of the present invention in form of a liquid or solid colorant composition separately to the tablet coating mixture or by adding a colorant composition to one of the components of the tablet coating mixture. Coloured hard or soft-shell capsules can be prepared by incorporating a colorant composition in the aqueous solution of the capsule mass.

Pharmaceutical compositions such as tablets such as chewable tablets, effervescent tablets or filmcoated tablets or capsules such as hard shell capsules wherein the compositions are used as an active ingredient are also within the scope of the present invention. The compositions of the present invention are typically added as powders to the tableting mixture or filled into the capsules in a manner per se known for the production of capsules.

Animal feed products such as premixes of nutritional ingredients, compound feeds, milk replacers, liquid diets or feed preparations wherein the compositions are either used as a colorant for pigmentation e.g. for egg yolks, table poultry, broilers or aquatic animals (especially shrimps, salmon, rainbow trout) or as an active ingredient are also within the scope of the present invention.

Personal care compositions: Cosmetics, toiletries and derma products i.e. skin and hair care products such as creams, lotions, baths, lipsticks, shampoos, conditioners, sprays or gels wherein the compositions are used as a colorant or as an active ingredient are also within the scope of the present invention.

The present invention is further illustrated by the following examples.

EXAMPLES

The following abbreviations are used:
DH=degree of hydrolysis
DI water=deionized water
dw=dry weight basis
RH=relative humidity
rpm=rounds per minute
SDS=sodium dodecyl sulfate
w/v=weight/volume Rice flour made from long grain rice was provided by Riceland Foods (Stuttgart, Ark.). Whey protein isolate was obtained from Biozate®, Davisco Foods International, INC., Minnesota as benchmark standard protein containing 88.6% protein (N×6.25) on dry weight basis. Alcalase 2.4 L, bacterial serine protease from *Bacillus licheniformis*, was provided by Novo Nordisk Biochem., (Franklinton, N.C., 2.4 AU units/g). Analytical reagents were purchased from Fisher Scientific (Pittsburgh, Pa.) and Sigma chemical Co. (St. Louis, Mo.).

(A) Analytical Methods: Examples 1-5

Example 1

Determination of Emulsion Activity and Emulsion Stability

The emulsion activity and stability was determined by the turbidimetric method of Pearce and Kinsella, Journal of Agric Food Chem. 1978, 26, 716-722. A mixture of 6 mL of a 0.1% solution of the rice endosperm protein in 10 mM phosphate buffer of a pH of 7.0 and 2 mL of corn oil was homogenized for 1 minute with a sonicator at setting 6 (Virtishear Tempest, The Virtis Co., Gardiner, N.Y., U.S.A.). 50 microliters of the mixture were transferred into 5 mL of an 0.1% aqueous solution of SDS (w/v) 0 and 10 minutes after the homogenization. The absorbance of the solution at 500 nm was determined with a spectrometer (Shimadzu Model UV-1601, Kyoto, Japan). The absorbance at the time 0 after homogenization is the emulsion activity of the rice endosperm protein. The decrease in turbidity (absorbance) of the initial absorbance during the time interval (10 min) was used to calculate the emulsion stability. (ES) was calculated as follows:

Emulsion Stability=$T_0 \times \Delta t / \Delta T$ where, $\Delta T$ is the decrease in turbidity (absorbance) of the initial absorbance (To) during the time interval of $\Delta t$ (10 min).

Example 2

Determination of the Degree of Hydrolysis

The DH was determined by the method of Nielsen and others (Nielsen, P. M., Petersen, D. & Dambmann, C.: Improved method for determining food protein degree of hydrolysis. Journal of Food Science 2001, 66 (5), 642-646). The o-phthaldialdehyde (OPA) reagent was prepared as follow: 7.620 g of di-sodium tetraborate decahydrate ($Na_2B_4O_7 \cdot 10H_2O$) and 200 mg sodium dodecyl sulfate (SDS) were dissolved in 150 mL of deionized water and then mixed with 160 mg of OPA (97% OPA pre-dissolved in 4 mL of ethanol) and 176 mg of 99% dithiothreitol (DTT). The final solution was made up to 200 mL with deionized water. Freeze dried protein sample of 0.1 g was solubilized in 10 mL deionized water. To measure the absorbance, 3 mL of OPA reagents was added to 10 mL tubes and then 400 µl of sample solution, serine standard (10 mg/100 mL) and deionized water was added in four tubes for each sample, standard and blank, respectively. This was followed by mixing for 5 and held for exactly 2 min. Absorbance was read at 340 nm with a spectrophotometer (Shimadzu Model UV-1601, Kyoto, Japan). The DH was calculated as follows.

$DH = h/h_{total} * 100\%$;

where h is the number of hydrolyzed bonds and $h_{total}$ is the total number of peptide bonds per protein equivalent; h=(Serine-NH2-β)/α equiv/g protein; where h is the number of hydrolyzed bonds and $h_{total}$ is the total number of peptide bonds per protein equivalent; for cereal protein α is 1.00, β is 0.40, and $h_{total}$ is 8.0.

Serine-NH2=$[(A_{340sample} - A_{340blank})/(A_{340standard} - A_{340blank})] * 0.9516$ meqv/L*0.01*100/(X*P);

where serine-NH2=meqv serine NH2/g protein; X=g sample; P=% protein in sample; 0.01 is the sample volume in liter (L).

Example 3

Determination of the Protein and Total Solubility

Protein solubility (also N-solubility) was determined by the method of Bera and Mukherjee (Bera, M. B., Mukherjee, R. K.: Solubility, emulsifying, and foaming properties of rice bran protein concentrates. J Food Sci 1989, 54(1), 142-145) with some modifications. 200 mg of protein sample was dispersed in 10 mL of deionized water, the pH was adjusted to 7.0 by 1 N HCl or 1 N NaOH. The dispersion was stirred continuously for 30 min and centrifuged at 5000 rpm for 15 min. (model J2-21, Beckman, Fullerton, Calif., U.S.A.). The supernatant was recovered, and the protein content in the supernatant was determined by the Automatic Kjeldahl method (AACC 1990). The percentage of protein solubility was calculated by following equation:

$$\text{Protein Solubility (\%)} = \frac{\text{Protein content of the supernantant}}{\text{Protein in 200 mg protein-isolate}} \times 100$$

The protein solubility was calculated as the percent ratio of protein in the supernatant to that of the total protein in the initial sample.

The total solubility was determined by oven drying method, and expressed as the percent ratio of total soluble portion of the supernatant to that of the total weight of the protein isolate.

$$\text{Total Solubility (\%)} = \frac{\text{Soluble portion of the supernatant}}{\text{200 mg protein-isolate}} \times 100$$

Example 4

Determination of Viscosity

Viscosity of the protein isolates was determined by a rotational rheometer (Haake VT 550, Germany) equipped with a MVDIN measuring spindle (radius=19.36 mm, height=58.08 mm) at room temperature (26° C.). The protein isolates were mixed with deionized water to form slurry of 10%, and the slurry was left for 60 min for equilibrium before analysis. The samples (30 ml) were loaded into the cylindrical cup (radius=21.0 mm) and were subjected to a shear rate that changed from 0 to 400 l/s over 3 min using a computer-controlled program. The data were analyzed by Rheowin Pro Data manager version 2.84 (Haake Mess Tech, Germany).

Example 5

Determination of the Protein Content

The protein contents were determined by an Automatic Kjeldahl method (AACC, 1990). The Kjeldahl 2006 Digester (Foss Tecator, Hoganas, Sweden) was used for digesting the samples in concentrated sulfuric acid with Kjeldahl® tablet as catalyst at 420° C. for 1 hour, and a Kjeltec® 2300 Analyzer Unit (Foss Tecator, Hoganas, Sweden) was used to determine the nitrogen content of the products. The protein contents were automatically calculated by multiplying the nitrogen content by a factor of 5.95.

(B) Manufacture of Rice Endosperm Protein Isolates (RP) (Starting Material and Comparison Example)

Example 6

One kilogram of rice flour was homogenized with 8 L deionized water (1:8, w/v) in a homogenizer (Virtishear Tempest, The Virtis Co., Gardiner, N.Y., USA) for 1 minute. The pH of the slurry was adjusted to 11.0 by 1 M NaOH, and the suspension was stirred for 3 hours at 40° C. The soluble protein in the solution was separated by centrifugation (5,000 rpm, 15 minutes). This procedure was repeated once to extract additional protein from the residue. Proteins in the combined supernatants of first and second extractions were isoelectrically precipitated at pH 4.5 and kept at 4° C. for 1 hour. The precipitate was recovered by centrifugation at 5,000 rpm for 20 minutes, washed with deionized water (1:4, w/v, pH 4.5), adjusted to pH 7.0. The extracted proteins (RP) were used as a starting material for the preparation of the following modifications (C) and (D).

Experimental Design of Examples (C), (D) and (E)

The present study includes two sets of experiments: (1) optimization rice protein glycosylation and, (2) comparison of controlled glycosylation, deamidation, and alcalase modification methods (comparison examples) on rice protein physicochemical properties. The optimization of glycosylation experiment was conducted in a 2×7 two factor factorial design (glucose and Xanthan gum) with repeated measurements (7 reaction-times) with 3 replicates. The comparison of glycosylation, deamidation, and alcalase modification methods were conducted in one factor completely randomized design, which included control (unmodified) rice protein and bench mark whey protein to evaluate and compare the effectiveness of the selected modification methods.

Thus, the rice endosperm protein was modified by the following methods: (1) Glycosylation of rice endosperm protein with D-glucose ($RP_{Glu}$); (2) Glycosylation of rice endosperm protein with Xanthan gum ($RP_{XG}$); (3) Deamidation of rice endosperm protein using alkali treatment ($RP_{DA}$); (4) Treatment of rice endosperm protein with alcalase to 1.8% DH ($RP_{Alc}$). The physicochemical and functional properties of the protein derivatives were evaluated and compared with those of unmodified rice endosperm protein (RP) and as bench mark compared with whey protein isolates.

(C) Manufacture of a Partially Hydrolyzed Rice Endosperm Protein

Example 7

(Comparison Example): Treatment of Rice Endosperm Protein with Alcalase to 1.8% DH($RP_{Alc}$)

The conditions for alcalase treatment were chosen based on a previous study (Paraman et al 2007) and our preliminary data. The rice endosperm protein isolate (RP) was homogenized with DI water (8% w/v) and, adjusted to pH 6.5. The protein colloidal solution was treated with 0.1% alcalase at 40° C. for 8.5 minutes. The enzyme was inactivated at 85° C. for 7 minutes. The hydrolysate was cooled immediately to 30° C. by adding ice, and the pH was readjusted to 7.0. The protein hydrolysate was spray dried and stored at 5° C. in air tight containers until they were used ($RP_{Alc}$).

(D) Manufacture of a Rice Endosperm Protein Partially Conjugated with Mono- or Polysaccharides Example 8

Evaluation of Optimal Reaction Conditions for the Partial Glycosylation of Rice Endosperm Protein The extracted rice protein RP (20 g on dw) was dissolved in deionized water to give a 10% (w/v) protein colloidal solution. D-glucose (0.465 g) dissolved in 10 mL DI water was added into the protein solution while stirring the protein solution at 37° C. The protein-glucose mixture was adjusted to pH 8.0 and stirred for 1 h at 37° C. The mixture was freeze-dried and the dried protein-sugar mixture was placed in aluminum plate, and incubated at 50° C. in an incubator maintained at 65% relative humidity. Approximately, 2.5 g of the protein-glucose mixture were drawn as samples at 4 hours intervals for 24 hours. The glycosylated protein was stored at 5° C. in air tight containers until they were used.

Rice protein-Xanthan gum optimization was conducted essentially similar to the method of protein-glucose optimization described above except for the following changes; the protein-Xanthan gum ration was 100:1, and the pH of the protein-Xanthan gum solution was adjusted to a value of 7.0.

Example 9

Glycosylation of Rice Endosperm Protein with D-Glucose ($RP_{Glu}$)

Glycosylation was conducted based on above optimization and the conditions chosen from literature (Kato at al 1990, Kato at al 1991, Achouri et al 2005, Oliver et al 2006) with some modifications as described below. The alkali extracted rice protein isolates RP (200 g on dw) were dissolved in water to give a 10% (w/v) protein colloidal solution. D-glucose (4.65 g) dissolved in 100 mL DI water was added to the protein solution while stirring the protein solution at 37° C. The protein-glucose mixture was adjusted to pH 8.0 and stirred for 1 hour at 37° C. The mixture was spray-dried and stored at 5° C. in air tight containers until they were used. The spray-dried protein-sugar mixture was placed in aluminum plate and incubated for 8 hours at 50° C. and 65% RH. The glycosylated protein (RPGlu) was stored at 5° C. until its use.

Example 10

Glycosylation of Rice Endosperm Protein with Xanthan Gum ($RP_{XG}$)

The rice endosperm protein isolate (RP) 200 g, on dw basis, was dissolved in water to give a 10% (w/v) protein colloidal solution. Xanthan gum (2 g) was dissolved separately in water to give 1% (w/v) xanthan-gum solution. The xanthan gum solution was added into the protein solution while stirring the protein solution at 37° C. The protein-xanthan gum mixture was spray-dried, and stored at 5° C. in air tight containers until they were used. The spray-dried protein-Xanthan gum mixture was placed in aluminum plate and incubated for 20 hours at 50° C. and 65% RH. The glycosylated protein ($RP_{XG}$) was stored at 5° C. until analyzed.

Example 11

Glycosylation of Rice Endosperm Protein with Potato Dextrin ($RP_{PD}$)

The rice endosperm protein isolate (RP) 200 g, on dw basis, was dissolved in water to give a 10% (w/v) protein colloidal solution. Potato dextrin (2 g) was dissolved separately in water to give 1% (w/v) potato dextrin solution. The potato dextrin solution was added into the protein solution while stirring the protein solution at 37° C. The protein-dextrin mixture was adjusted to pH 7.0, stirred for 1 hour at 37° C., spray-dried, and stored at 5° C. in air tight containers until they were used. The spray-dried protein-dextrin mixture was placed in aluminum plate and incubated for 20 hours at 50° C. and 65% RH. The glycosylated protein ($RP_{PD}$) was stored at 5° C. until analyzed.

Example 12

Glycosylation of Rice Endosperm Protein with Cyclodextrin ($RP_{CD}$)

The rice endosperm protein isolate (RP) 200 g, on dw basis, was dissolved in water to give a 10% (w/v) protein colloidal solution. Cyclodextrin (2 g) was dissolved separately in water to give 1% (w/v) cyclodextrin solution. The cyclodextrin solution was added into the protein solution while stirring the protein solution at 37° C. The protein-cyclodextrin mixture was adjusted to pH 7.0, stirred for 1 hour at 37° C., spray-dried, and stored at 5° C. in air tight containers until they were used. The spray-dried protein-cyclodextrin mixture was placed in aluminum plate and incubated for 20 hours at 50° C. and 65% RH. The glycosylated protein ($RP_{CD}$) was stored at 5° C. until analyzed.

Example 13

Glycosylation of Rice Endosperm Protein with Pectin ($RP_P$)

The rice endosperm protein isolate (RP) 200 g, on dw basis, was dissolved in water to give a 10% (w/v) protein colloidal solution. Pectin (2 g) was dissolved separately in water to give 1% (w/v) pectin solution. The pectin solution was added into the protein solution while stirring the protein solution at 37° C. The protein-pectin mixture was adjusted to pH 7.0, stirred for 1 hour at 37° C., spray-dried, and stored at 5° C. in air tight containers until they were used. The spray-dried protein-pectin mixture was placed in aluminum plate and incubated for 20 hours at 50° C. and 65% RH. The glycosylated protein ($RP_P$) was stored at 5° C. until analyzed.

(E) Manufacture of a Partially Deamidated Rice Endosperm Protein

Example 14

Deamidation of Rice Endosperm Protein using Alkali Treatment ($RP_{DA}$)

The deamidation conditions were chosen based on literature information (Schwenke 1997, Cabra et al 2007) with some modifications as described below. Alkali extracted rice protein isolate was mixed with DI water (8% w/v). The protein colloidal solution was adjusted to pH 11.0 and stirred at 25° C. for 12 hours. Then, the temperature of the protein solution was increased under stirring for 30 min at 70° C. The solution was cooled immediately to 30° C. by adding ice, and the pH was readjusted to 7.0. The deamidated protein solution was spray dried, and stored at 5° C. ($RP_{DA}$).

(F) Results

Statistical Analysis

All the experiments were conducted in duplicate. Data were analyzed for variance and multiple mean comparisons with JMP 6 software (SAS Inst 2002). The significance of difference between means was determined by the Tukey HSD procedure at the 5% significance level (P<0.05).

Optimization of the Glycosylation of Rice Endosperm Protein

The glycosylation of rice protein with D-glucose and Xanthan gum were optimized as described above. The solubility and emulsifying properties of the glycosylated proteins are presented in Table 3.

TABLE 3

Solubility and emulsifying properties of D-glucose and Xanthan gum glycosylated rice protein as a function of incubation time at 50° C. and 65% relative humidity

| Glycosylation treatments: | D-glucose glycosylated rice protein | | | Xanthan gum glycosylated rice protein | | |
|---|---|---|---|---|---|---|
| Reaction time (h = hour(s)) | Solubility (%) | Emulsion activity ($A_{500}$) | Emulsion stability (min) | Solubility (%) | Emulsion activity ($A_{500}$) | Emulsion stability (min) |
| RP-control | 18.0 | 0.266 | 14.7 | 18.0 | 0.266 | 14.7 |
| RP-0 h | 23.6 | 0.371 | 15.4 | 26.1 | 0.479 | 18.1 |
| RP-4 h | 28.9 | 0.707 | 20.4 | 27.0 | 0.497 | 20.8 |
| RP-8 h | 34.4 | 0.712 | 23.4 | 30.0 | 0.515 | 24.5 |
| RP-12 h | 33.5 | 0.627 | 25.4 | 32.3 | 0.523 | 24.0 |
| RP-16 h | 29.7 | 0.601 | 26.8 | 33.1 | 0.583 | 25.5 |
| RP-20 h | 28.3 | 0.462 | 27.2 | 31.8 | 0.629 | 26.4 |
| RP-24 h | 24.3 | 0.350 | 28.0 | 33.0 | 0.632 | 27.0 |

Glycosylation of rice protein D-glucose (2.25%, w/w) and rice protein-Xanthan gum (1%, w/w) conjugates were prepared at 50° C. and 65% relative humidity for varying incubation time (0-24 hours). Since the reaction starts very fast, even at the beginning a difference compared to untreated rice endosperm protein isolate was recognized.

The functional properties of the glycosylated proteins differed significantly as a function of Maillard reaction time and depended on the type of sugar used to glycosylate the protein. For D-glucose, the optimum Maillard reaction time was 8 hours at 50° C. and 65% RH. The glycosylated proteins demonstrated a gradual improvement in solubility and emulsifying properties as a function of Maillard reaction up to 8 hours. This trend was illustrated by an increase in solubility from 23% to 34%, and the emulsion activity from 0.371 to 0.712 as reaction time progressed from 0 hours to 8 hours. These properties decreased beyond 8 hours of incubation. However, the emulsion stability of the glycosylated proteins gradually increased from 15.4 to 28 minutes, as the function of incubation time from 0 to 24 hours. The increment of emulsion stability was higher at the early stage of incubation (0-12 hours) than that of the late stage (12-24 hours), which might be due to decreasing availability of amino groups with progressing Maillard reaction.

In Xanthan gum glycosylated proteins, the solubility and emulsifying properties gradually increased up to 16 and 20 hours, respectively. The solubility increased from 26% to 33% in 16 hours incubation; the emulsifying activity increased from 0.479 to 0.629 in 20 hours of incubation. Compared to glucose, Xanthan gum mediated glycosylation improved the functional properties at a slower rate and required more time for Maillard reaction. A 18-20 hour period of incubation was the optimum reaction time for Xanthan gum at 50° C., 65% RH, and 1:100 Xanthan gum to protein ratio. The optimum reaction time varied and depended on the reactants and reaction conditions (Oliver 2006). Simple sugars can react faster and required shorter duration than polysaccharides.

In the present study, the optimal reaction times were much shorter than the studies published previously. Lysozyme glycosylated with Xanthan gum demonstrated superior emulsifying properties after 7 days of Maillard reaction (Nakamura et al 2000). Similarly, Ovalhumin conjugated with glucose reached maximum emulsion activity in 1 day and emulsion stability in 14 days of reaction time (Kato et al 1995). The differences in time requirement might be due to the differences in pre-incubation conditions used in these experiments. For instance, in these two previous studies, protein-sugar mixture was adjusted to pH 7.0 and immediately freeze-dried. However, in the present study, the protein-sugar mixture was stirred for 1 h before drying. The pH of the sugar-rice protein mixture was maintained at pH 8.0. The slight alkali condition (pH 8.0) and longer mixing condition (1 hour) might have facilitated Maillard reaction in the liquid stage.

The solubility and emulsifying data of native and glycosylated protein with 0 h incubation supported this presumption (Table 3). The solubility and emulsifying properties of glycosylated protein with 0 hour incubation showed higher solubility and emulsifying properties than that of native rice protein controls. For glucose-rice protein conjugate, the solubility improved from 18 to 24% and emulsion activity improved from 0.266 to 0.371 without any dry-stage reaction (Table 3); for Xanthan gum-rice protein conjugate, the solubility increased from 18 to 26%, emulsion activity and stability increased from 0.266 to 0.479 and from 14.7 to 18.1 min, respectively.

In Glycosylation Cross-Linking Study, Preliminary Experiments were Conducted with D-Glucose, Potato-Dextrin, Cyclodextrin, Pectin, Xanthan Gum.

Based on our preliminary data presented in (Table 4), D-glucose and Xanthan gum conjugation significantly improved both solubility and emulsifying properties compared to rice endosperm protein and potato-dextrin, cyclodextrin, or pectin conjugated rice protein. Thus, D-glucose and Xanthan gum were selected for further process optimization of glycosylation.

Potato-dextrin, cyclodextrin and pectin conjugation did not improve the endosperm protein solubility, but slightly improved the emulsifying properties compared to control rice endosperm protein.

TABLE 4

Solubility and emulsifying properties office endosperm protein glycosylated with various carbohydrates at 50° C. and 65% relative humidity for 12 and 24 hours

| Type of carbohydrate | Incubation time (h) | Solubility (%) | Emulsion activity ($A_{500}$) | Emulsion stability (min) |
|---|---|---|---|---|
| Control rice protein | | 17.4 | 0.259 | 15.8 |
| D-glucose | 12 | 31.4 | 0.596 | 23.1 |
| D-glucose | 24 | 26.7 | 0.417 | 26.2 |

TABLE 4-continued

Solubility and emulsifying properties office endosperm protein glycosylated with various carbohydrates at 50° C. and 65% relative humidity for 12 and 24 hours

| Type of carbohydrate | Incubation time (h) | Solubility (%) | Emulsion activity ($A_{500}$) | Emulsion stability (min) |
|---|---|---|---|---|
| Potato-dextrin | 12 | 16.1 | 0.367 | 18.6 |
| Potato-dextrin | 24 | 17.9 | 0.339 | 20.4 |
| Cyclodextrin | 12 | 14.8 | 0.317 | 24.3 |
| Cyclodextrin | 24 | 11.8 | 0.294 | 22.5 |
| Pectin | 12 | 14.1 | 0.266 | 15.8 |
| Pectin | 24 | 13.7 | 0.386 | 17.9 |
| Xanthan gum | 12 | 29.7 | 0.509 | 22.6 |
| Xanthan gum | 24 | 35.7 | 0.577 | 28.3 |

The protein:carbohydrate ratios used in this experiment were 100:2.265 for glucose, and 100:1 for potato-dextrin, Cyclodextrin, pectin, and Xanthan gum.

The optimized glycosylated rice proteins were further compared and evaluated for physicochemical and functional properties of the proteins modified by controlled enzymatic hydrolysis and alkali deamidation. The treatments and brief methods of modification are summarized in Table 5.

TABLE 5

Summary office protein modification methods

| Rice protein isolate type | | Brief out line of rice endosperm protein preparation |
|---|---|---|
| $RP_{Control}$ | RP | Rice endosperm protein with no further modification |
| $KP_{Alcalase}$ | $RP_{Alc}$ | Alcalase treated rice endosperm protein to 1.8% DH |
| $RP_{Glucose}$ | $RP_{Glu}$ | Glycosylated rice endosperm protein with D-Glucose |
| $RP_{Xanthan\ Gum}$ | $RP_{XG}$ | Glycosylated rice endosperm protein with Xanthan gum |
| $RP_{Deamidation}$ | $RP_{DA}$ | Alkali deamidated rice endosperm protein |

The rice endosperm protein was modified by the above methods: (1) Glycosylation of rice endosperm protein with D-glucose ($RP_{Glu}$); (2) Glycosylation of rice endosperm protein with Xanthan gum ($RP_{XG}$); (3) Deamidation of rice endosperm protein using alkali treatment ($RP_{DA}$); (4) Treatment of rice endosperm protein with alcalase to 1.8% DH ($RP_{Alc}$) to improve the solubility and emulsifying properties Influence of Controlled Glycosylation, Deamidation, and Alcalase Modifications on Rice Protein physicochemical and Functional Properties Physicochemical Properties Protein and moisture content of the rice protein products are presented in Table 6.

TABLE 6

Moisture, protein content, and viscosity of rice protein isolates modified by control enzymatic hydrolysis, glycosylation and deamidation

| Rice protein isolate type | pH (as is) | Moisture % | Protein (as is, %) | Protein (%) (Dry weight basis) | Viscosity (mPas)* |
|---|---|---|---|---|---|
| $RP_{Control}$ | 7.1 | 2.7 | 84.6 | 86.7 | 8.7 |
| $RP_{Alcalase}$ | 7.4 | 3.3 | 83.7 | 86.5 | 7.0 |
| $RP_{Glucose}$ | 6.9 | 8.8 | 77.4 | 84.9 | 12.4 |
| $RP_{Xanthan\ Gum}$ | 6.8 | 9.0 | 75.9 | 83.4 | 31.6 |
| $RP_{Deamidation}$ | 6.9 | 4.5 | 74.2 | 77.6 | 14.0 |
| Whey protein | 8.4 | 3.9 | 85.2 | 88.6 | 5.6 |

Values are means of duplicates and expressed on dry weight basis. Mean values with different letters in the same column are significantly different ($P < 0.05$).
*Viscosity at 26° C., at constant shear rate of 400 $s^{-1}$; 1 Pas (Pascal second) = 1000 cP (centipoises = mPas); Viscosity was measured on 'as is' basis.

The glycosylated proteins, $RP_{Glu}$, $RP_{XG}$, contained higher moisture content (8.8-9.0%) than that of other proteins. These two products, $RP_{Glu}$, $RP_{XG}$, absorbed moisture during the glycosylation process that was carried out at 65% RH for 8 and 18 hours, respectively. Protein content of the glycosylated proteins ($RP_{Glu}$, $RP_{XG}$) did not differ from the control rice protein isolates (RP) as low percent of glucose (2.25%, w/w) and Xanthan gum (1%, w/w) were used to glycosylate the proteins.

Figure 1:
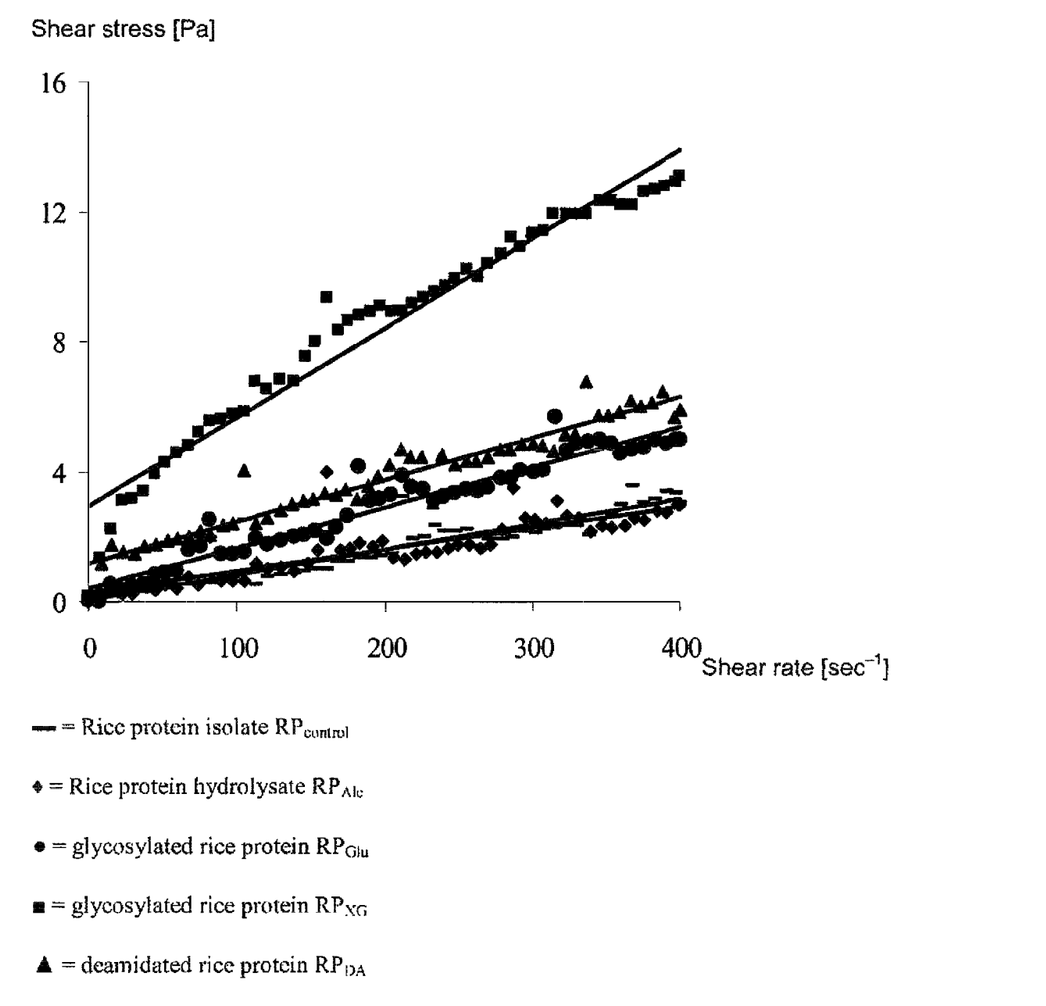
FIG. 1 shows the relationship between shear stress (y-axis; in Pa) and shear rate (x-axis; in $sec^{-1}$) for rice protein isolates (■$RP_{control}$)) hydrolysate (♦$RP_{Alc}$), glycosylated (●$RP_{Glu}$ and ■$RP_{XG}$), and deamidated (▲$RP_{DA}$) rice protein at 10% w/v concentration; 1 Pas (Pascal second)=1000 cP (centipoises=mPas). The viscosity was the slope of shear stress and shear rate of the linear line.

The viscosity of the protein proteins are presented in Table 6 and FIG. 1.

Glycosylated ($RP_{Glu}$, $RP_{XG}$) and deamidated ($RP_{DA}$) proteins showed much higher viscosity than the protease treated ($RP_{Alc}$) and control rice proteins (RP). The increased viscosity can be an indication of increasing hydrophilicity of the glycosylated. Particularly, glycosylation with Xanthan gum increased the viscosity of the product to 31.6 mPas, which was significantly higher than that of glucose mediated glycosylation (12.4 mPas) and deamidation (14.0 mPas) methods. The higher viscosity of Xanthan gum conjugated protein might be due the complex size of the glycosyl residue. In general, increasing viscosity of glycosylated proteins indicated the structural changes in protein. Glycosylated proteins have greater hydrodynamic volume and increases hydration properties due to the increase of surface hydrophilicity and partial unfolding of quaternary structure of protein (Baniel et al 1992).

The deamidation also increased the viscosity from 8.7 to 14.0 mPas. This indicated the improved hydration properties of the deamidated proteins. Deamidation of amide groups into carboxyl groups might possibly alter the charge content of the protein and improved the interaction of protein with water molecules. However, considering the condition use to perform the deamidation, it is obvious that the viscosity of the deamidated protein was the net result of deamidation, denaturation, and peptide bond cleavage.

The alcalase treatment reduced the viscosity slightly from 8.7 to 7.0 mPas in $RP_{Alc}$. The reduction in viscosity was due to the reduction of protein molecular size. However, the viscosity change was small, since the protein hydrolysis was controlled to 1.8% DH.

Protein Solubility

The solubility and emulsifying properties of the proteins are presented in Table 7.

TABLE 7

Nitrogen solubility and emulsifying properties of the rice protein isolates

| Rice protein isolates | Degree of hydrolysis (DH)* | N solubility (%) | Emulsion activity (A500) | Emulsion stability (min) |
|---|---|---|---|---|
| $RP_{Control}$ | — | 18.0 | 0.266 | 14.7 |
| $RP_{Alcalase}$ | 1.8 | 33.3 | 0.468 | 17.5 |
| $RP_{Glucose}$ | — | 39.7 | 0.721 | 26.8 |
| $RP_{Xanthan\ Gum}$ | — | 38.6 | 0.661 | 26.1 |

TABLE 7-continued

Nitrogen solubility and emulsifying properties of the rice protein isolates

| Rice protein isolates | Degree of hydrolysis (DH)* | N solubility (%) | Emulsion activity (A500) | Emulsion stability (min) |
|---|---|---|---|---|
| $RP_{Deamidation}$ | — | 68.3 | 0.776 | 24.0 |
| Whey protein | — | 97.2 | 0.952 | 18.8 |

Values are means of duplicates and expressed on dry weight basis. Mean values with different letters in the same column are significantly different (P < 0.05).
*DH values are presented only with the samples that were subjected to protease treatments.

Glycosylation with glucose and Xanthan gum increased the solubility of rice protein to ~40%, however, the increment of solubility by glycosylation was not substantial to the level expected.

Alcalase treatment (1.8%, DH) improved the solubility from 18% to 33%. The increasing solubility was due to decreasing molecular size and increasing number of polar groups (Nielsen 1997). A previous study reported that a high percent of the rice protein remained insoluble even after 13.5% DH by alcalase enzyme (Paraman et al 2007), which suggested that the either peptides cleaved by proteases were associated with unhydrolyzed protein via inter molecular hydrophobic or sulfhydryl interactions or the amorphous regions of the protein only accessible to hydrolysis.

The deamidated protein showed higher solubility (68%) than any other treatments (28-39%). The deamidated protein showed 68.3% solubility. The deamidation in alkali condition might have deamidated the side chain amide group of the aspartic and glutamic amino acids and possibly alerted the protein polarity. Deamidation increase the negative charge and can disrupt hydrophobic and hydrogen bonds (Schwenke 1997). These structural changes can contribute to an increase in solubility. Particularly, the most abundant amino acids in rice glutelin are glutamine, asparagine, arginine, glycine, and alanine (Wen and Luthe 1985). Deamidation of these amino acid residues can facilitate protein solubility, and contributed to an improvement in emulsifying properties. Further, partial cleavage of peptide bonds could be possible in the deamidation process. The combined effect of hydrolysis along with deamidation might have contributed to the great improvement of solubility.

Emulsifying Properties

The emulsion activity and stability of the glycosylated and deamidated proteins were significantly higher than that of protease treated rice protein isolates. The glycosylated protein with glucose showed 0.721 emulsion activity and 26.8 min emulsion stability. The deamidated protein showed 0.776 emulsion activity and 24.0 min emulsion stability. The emulsifying properties of these two protein isolates are higher than that of unmodified and protease modified rice protein isolates. Glycosylation makes the proteins more hydrophilic (Kato et al 1991). Therefore, controlled and limited glycation improves emulsifying properties. Increasing hydrophilic nature improves the hydration and solubility and thus possibly opens up the globular structure of protein. The partial unfolding could have improved the ability of the glycosylated protein to form stable interfacial film at the oil-water interface.

In the case of deamidated protein, improvement in emulsion properties may be attributed by increasing protein solubility and polarity (Schwenke 1997). In addition to deamidation, as discussed earlier, the partial cleavage of peptide bond also might have contributed to the improvement of solubility and emulsifying properties. Increased solubility of the deamidated protein might help produce stable interaction at the oil-water interface and thus improved the emulsifying properties. The proper balances of deamidation and peptide bond cleavage might be the key in improving the emulsion properties rice protein by deamidation.

The alcalase treatment to 1.8% DH(RP$_{Alc}$) improved emulsion activity from 0.266 to 0.468, and emulsion stability from 17.7 to 17.5 min compared to unmodified rice protein (RP). In general, a low degree of hydrolysis is recommended to improve the functionality of food proteins, especially emulsion stability. Limited proteolysis could improve molecular flexibility and hydrophobic-hydrophilic balance of protein which resulting better emulsification (Nielsen 1997; Schwenke 1997). However, the limited improvement of solubility and emulsifying properties might be due to (1) high hydrophobic and sulfhydryl interactions, and exposure of buried hydrophobic regions of protein that accompanied high temperature enzyme inactivation may have promoted aggregation and cross linking of partially hydrolyzed proteins (Paraman et al 2007). Further, due to the compact nature of the protein, the enzyme alcalase might have a limited access to interior peptide bonds, which could possibly lead to the formation of uneven size of peptide and decrease the emulsifying properties of the resulting hydrolysate.

CONCLUSION

To improve the solubility and emulsifying properties of rice endosperm protein, glycosylation and deamidation type modifications were more effective than proteolysis modification by alcalase to 1.8% DH. In rice endosperm protein glycosylation, the optimum Maillard reaction time was 8 h and 20H at 50° C. and 65% RH for D-glucose and Xanthan gum, respectively. The deamidated protein showed the highest solubility (68%) and emulsifying properties (0.776-emulsion activity, 24 min emulsion stability) among the proteins evaluated in this study. The controlled enzymatic hydrolysis by alcalase 1.8% DH only improved emulsion activity from 0.266 to 0.468, and emulsion stability from 14.7 to 17.5 min compared to unmodified rice protein (RP). The highest solubility and emulsifying properties of deamidated protein were the net result of deamidation, peptide bond cleavage, and protein denaturation that took place in the process of deamidation.

(G) Manufacture of a Composition of a Fat-Soluble Active Ingredient or a Fat-Soluble Colorant According to the Present Invention Example 15

Manufacture of a Formulation of Vitamin E (Acetate)

A formulation comprising a rice endosperm protein and vitamin E may be prepared as follows:
a) Preparation of an Emulsion:
20 g of RP$_{Glu}$ (Glycosylation of rice endosperm protein with D-glucose) according to Example 9 were mixed with 60 g of sucrose and re-dissolved in 140 ml of water by stirring at 75° C. for 15 minutes. 88.3 g of dl-α tocopherol acetate were heated to 70° C. and under vigorous stirring added to the aqueous solution. The dispersion was vigorously stirred for another 15 minutes. Under gently stirring further 225 mL of water were added and the so-obtained emulsion was characterised with respect to the particle size of the inner phase. The mean particle size (Sauter diameter, D[3, 2]) of the inner phase of the emulsion was 1.86 μm as measured by laser diffraction (Malvern Masersizer). After storage for 12 hours, the emulsion was again characterised with respect to the particle size of the inner phase. The mean particle size (Sauter diameter, D[3, 2]) of the inner phase of the emulsion after storage was 1.81 μm as measured by laser diffraction (Malvern Masersizer).
b) Preparation of a Solid Formulation from the Emulsion:
The emulsion may be sprayed into a pre-cooled fluidised bed of cornstarch. Excess cornstarch can be removed by sieving and the powder obtained can be dried in an air stream at room temperature. The powder particle fraction in the range of 0.16 to 0.63 mm can be collected by sieving Alternatively, the emulsion can be converted into a solid form by using further well known drying technologies such spray drying.

Example 16

Manufacture of a Formulation of Vitamin E (Acetate)

A formulation comprising a rice endosperm protein and vitamin E may be prepared as follows:
a) Preparation of an Emulsion:
20 g of RP$_{XG}$ (Glycosylation of rice endosperm protein with Xanthan gum) according to Example 10 were mixed with 60 g of sucrose and re-dissolved in 140 ml of water by stirring at 75° C. for 15 minutes. 83.2 g of dl-α tocopherol acetate were heated to 70° C. and under vigorous stirring added to the aqueous solution. The dispersion was vigorously stirred for another 15 minutes. Under gently stirring further 225 mL of water were added and the so-obtained emulsion was characterised with respect to the particle size of the inner phase. The mean particle size (Sauter diameter, D[3, 2]) of the inner phase of the emulsion was 1.65 μm as measured by laser diffraction (Malvern Masersizer). After storage for 12 hours, the emulsion was again characterised with respect to the particle size of the inner phase. The mean particle size (Sauter diameter, D[3, 2]) of the inner phase of the emulsion after storage was 1.64 μm as measured by laser diffraction (Malvern Masersizer).
b) Preparation of a Solid Formulation from the Emulsion:
The emulsion may be sprayed into a pre-cooled fluidised bed of cornstarch. Excess cornstarch can be removed by sieving and the powder obtained can be dried in an air stream at room temperature. The powder particle fraction in the range of 0.16 to 0.63 mm can be collected by sieving alternatively; the emulsion can be converted into a solid form by using further well known drying technologies such spray drying.

Example 17

Manufacture of a Formulation of Vitamin E (Acetate)

A formulation comprising a rice endosperm protein and vitamin E may be prepared as follows:
a) Preparation of an Emulsion:
20 g of RP$_{DA}$ (Deamidation of rice endosperm protein using alkali treatment) according to Example 14 were mixed with 60 g of sucrose and re-dissolved in 140 ml of water by stirring at 75° C. for 15 minutes. 81.9 g of dl-α tocopherol acetate were heated to 70° C. and under vigorous stirring added to the aqueous solution. The dispersion was vigorously stirred for another 15 minutes. Under gently stirring further 225 mL of water were added and the so-obtained emulsion was characterised with respect to the particle size of the inner phase. The mean particle size (Sauter diameter, D[3, 2]) of the inner phase of the emulsion was 1.77 μm as measured by laser diffraction (Malvern Masersizer). After storage for 12 hours, the emulsion was again characterised with respect to the particle size of the inner phase. The mean particle size (Sauter diameter, D[3, 2]) of the inner phase of the emulsion after storage was 1.68 μm as measured by laser diffraction (Malvern Masersizer).

b) Preparation of a Solid Formulation from the Emulsion:

The emulsion may be sprayed into a pre-cooled fluidised bed of cornstarch. Excess cornstarch can be removed by sieving and the powder obtained can be dried in an air stream at room temperature. The powder particle fraction in the range of 0.16 to 0.63 mm can be collected by sieving Alternatively, the emulsion can be converted into a solid form by using further well known drying technologies such spray drying.

Example 18

Manufacture of a Formulation of β-Carotene

A formulation comprising a rice endosperm protein and β-carotene may be prepared as follows:

a) Preparation of a(n Oil-Based) Solution 1:

6.6 g of corn oil and 1.2 g of dl-α-tocopherol were mixed. 13.8 g of crystalline n-carotene were dispersed in 180 ml of chloroform (trichloromethane) and the resulting dispersion was added to the mixture of corn oil and tocopherol. By gently stirring and simultaneous heating the mixture to about 60° C. a solution was obtained.

b) Preparation of a(n Aqueous) Solution 2:

30 g of $RP_{Glu}$ (Glycosylation of rice endosperm protein with D-glucose) according to Example 9 was re-dissolved in 120 ml of water by stirring at 60° C.

c) Preparation of an Emulsion from the Solutions 1 and 2:

Under vigorous stirring solution 1 was added to solution 2 at 53° C. and the dispersion was vigorously stirred for another 30 minutes. The stirred dispersion was kept at 50 to 55° C. for 30 minutes. Residual trichloromethane was removed at 50 to 55° C. After removing entrapped air bubbles by centrifugation the emulsion was gently stirred at 50 to 55° C. for some minutes and then characterised with respect to the particle size of the inner phase. The mean particle size (Sauter diameter, D[3, 2]) of the inner phase of the emulsion was 440 nm as measured by laser diffraction (Malvern Masersizer).

d) Preparation of a Solid Formulation from the Emulsion:

The emulsion may be sprayed into a pre-cooled fluidised bed of cornstarch. Excess cornstarch can be removed by sieving and the powder obtained can be dried in an air stream at room temperature. The powder particle fraction in the range of 0.16 to 0.63 mm can be collected by sieving and characterised with respect to the carotenoid content, the colour intensity and the colour hue in an aqueous dispersion, the content of the corn starch and residual humidity.

TABLE 8

Calculated composition of the dried formulation

| Compound | Amount [weight-%, based on the total dry weight] |
|---|---|
| $RP_{Glu}$: Rice endosperm protein according to example 9 | 25.0 |
| sucrose | 30.5 |
| ascorbyl palmitate | 1.5 |
| β-carotene | 11.5 |
| corn oil | 5.5 |
| dl-α-tocopherol | 1.0 |
| Corn starch fluid | 25.0 |

Example 19

Manufacture of a Formulation of β-Carotene

A formulation comprising a rice endosperm protein and β-carotene may be prepared as follows:

a) Preparation of a(n Oil-Based) Solution 1:

6.6 g of corn oil and 1.2 g of dl-α-tocopherol were mixed. 13.8 g of crystalline β-carotene were dispersed in 180 ml of chloroform (trichloromethane) and the resulting dispersion was added to the mixture of corn oil and tocopherol. By gently stirring and simultaneous heating the mixture to about 60° C. a solution was obtained.

b) Preparation of a(n Aqueous) Solution 2:

30 g of $RP_{XG}$ (Glycosylation of rice endosperm protein with Xanthan gum) according to Example 10 was re-dissolved in 120 ml of water by stirring at 60° C. Additionally 1.8 g of ascorbyl palmitate and 36.6 g of sucrose were added. 0.5 ml of aqueous 1 N NaOH were used to adjust the pH to a value of 7.3.

c) Preparation of an Emulsion from the Solutions 1 and 2:

Under vigorous stirring solution 1 was added to solution 2 at 53° C. and the dispersion was vigorously stirred for another 30 minutes. The stirred dispersion was kept at 50 to 55° C. for 30 minutes. Residual trichloromethane was removed at 50 to 55° C. After removing entrapped air bubbles by centrifugation the emulsion was gently stirred at 50 to 55° C. for some minutes and then characterised with respect to the particle size of the inner phase. The mean particle size (Sauter diameter, D[3, 2]) of the inner phase of the emulsion was 380 nm as measured by laser diffraction (Malvern Masersizer).

d) Preparation of a Solid Formulation from the Emulsion:

The emulsion may be sprayed into a pre-cooled fluidised bed of cornstarch. Excess cornstarch can be removed by sieving and the powder obtained can be dried in an air stream at room temperature. The powder particle fraction in the range of 0.16 to 0.63 mm can be collected by sieving and characterised with respect to the carotenoid content, the colour intensity and the colour hue in an aqueous dispersion, the content of the corn starch and residual humidity.

TABLE 9

Calculated composition of the dried formulation

| Compound | Amount [weight-%, based on the total dry weight] |
|---|---|
| $RP_{XG}$: Rice endosperm protein according to example 10 | 25.0 |
| sucrose | 30.5 |
| ascorbyl palmitate | 1.5 |
| β-carotene | 11.5 |
| corn oil | 5.5 |

TABLE 9-continued

Calculated composition of the dried formulation

| Compound | Amount [weight-%, based on the total dry weight] |
|---|---|
| dl-α-tocopherol | 1.0 |
| Corn starch fluid | 25.0 |

Example 20

Manufacture of a Formulation of β-Carotene

A formulation comprising a rice endosperm protein and n-carotene may be prepared as follows:
a) Preparation of a(n Oil-Based) Solution 1:
  6.6 g of corn oil and 1.2 g of dl-α-tocopherol were mixed. 13.8 g of crystalline β-carotene were dispersed in 180 ml of chloroform (trichloromethane) and the resulting dispersion was added to the mixture of corn oil and tocopherol. By gently stirring and simultaneous heating the mixture to about 60° C. a solution was obtained.
b) Preparation of a(n Aqueous) Solution 2:
  30 g of $RP_{DA}$ (Deamidation of rice endosperm protein using alkali treatment) according to Example 16 was re-dissolved in 120 ml of water by stirring at 60° C. Additionally 1.8 g of ascorbyl palmitate and 36.6 g of sucrose were added. 0.4 ml of aqueous 1 N NaOH were used to adjust the pH to a value of 7.0.
c) Preparation of an Emulsion from the Solutions 1 and 2:
  Under vigorous stirring solution 1 was added to solution 2 at 53° C. and the dispersion was vigorously stirred for another 30 minutes. The stirred dispersion was kept at 50 to 55° C. for 30 minutes. Residual trichloromethane was removed at 50 to 55° C. After removing entrapped air bubbles by centrifugation the emulsion was gently stirred at 50 to 55° C. for some minutes and then characterised with respect to the particle size of the inner phase. The mean particle size (Sauter diameter, D[3, 2]) of the inner phase of the emulsion was 500 nm as measured by laser diffraction (Malvern Masersizer).
d) Preparation of a Solid Formulation from the Emulsion:
  The emulsion may be sprayed into a pre-cooled fluidised bed of cornstarch. Excess cornstarch can be removed by sieving and the powder obtained can be dried in an air stream at room temperature. The powder particle fraction in the range of 0.16 to 0.63 mm can be collected by sieving and characterised with respect to the carotenoid content, the colour intensity and the colour hue in an aqueous dispersion, the content of the corn starch and residual humidity.

TABLE 10

Calculated composition of the dried formulation

| Compound | Amount [weight-%, based on the total dry weight] |
|---|---|
| $RP_{DA}$: Rice endosperm protein according to example 14 | 25.0 |
| sucrose | 30.5 |
| ascorbyl palmitate | 1.5 |
| β-carotene | 11.5 |
| corn oil | 5.5 |
| dl-α-tocopherol | 1.0 |
| Corn starch fluid | 25.0 |

The invention claimed is:

1. A process for the manufacture of a rice endosperm protein which is partially conjugated with glucose or Xanthan gum, whereby before milling the rice bran was removed, comprising the following steps a) to e):
  a) preparing an aqueous solution or suspension of milled rice, whereby the rice bran was removed before milling, whereby the solution or suspension has a dry mass content of from 0.1 to 30 weight-%, based on the total amount of the aqueous solution or suspension;
  b) removing the non-protein part of the milled rice, whereby the rice bran was removed before milling, to obtain the rice endosperm protein;
  c) modifying the rice endosperm protein part of the milled rice, whereby the rice bran was removed before milling, by reacting the rice endosperm protein part of the milled rice partially with glucose or Xanthan gum in a Maillard reaction to obtain rice endosperm protein which is partially conjugated with glucose or Xanthan gum;
  d) optionally isolating the rice endosperm protein which is partially conjugated with glucose or Xanthan gum;
  e) optionally converting the rice endosperm protein which is partially conjugated with glucose or Xanthan into a solid form.

2. The process according to claim 1, wherein the removal of the non-protein part (step b) is achieved by treating the milled rice with non-protein degrading enzymes, deactivating the enzymes, separating and removing the non-protein part from the protein part of the milled rice.

3. The process according to claim 2, wherein the non-protein degrading enzymes are starch-degrading enzymes, cellulose-degrading enzymes or mixtures thereof.

4. The process according to claim 2, wherein the separation of the non-protein part is achieved by centrifugation followed by washing off the non-protein part with water.

5. The process according to claim 1, wherein step e) is achieved by drying.

6. The process according to claim 5, wherein the reaction in step e) is by freeze drying or spray drying.

7. A rice endosperm protein which is partially reacted with glucose or Xanthan gum obtainable by the process according to claim 1.

8. A composition comprising a rice endosperm protein having an emulsion activity as determined turbidimetrically by emulsifying a 0.1% solution of a sample rice endosperm protein in corn oil, homogenized by sonication for one minute and measuring absorbance, the absorbance at a time 0 after homogenization indicating the emulsion activity of the rice endosperm of ≥0.6 and which is partially reacted with glucose or Xanthan gum and a fat-soluble active ingredient and/or a fat-soluble colorant.

9. The composition according to claim 8, wherein the fat-soluble active ingredient and/or the fat-soluble colorant is a carotene or a structurally related polyene compound, a fat soluble vitamin, a triglyceride rich in polyunsaturated fatty acids, an oil soluble UV-A filter, an UV-B filter or a mixture thereof.

10. The composition according to claim 9, wherein the carotene or structurally related polyene compound is a carotenoid selected from the group consisting of α-carotene, β-carotene, 8'-apo-β-carotenal, 8'-apo-β-carotenoic acid esters, canthaxanthin, astaxanthin, lycopene, lutein, zeaxanthin, crocetin, α-zeacarotene, β-zeacarotene and a mixture thereof.

11. The composition according to claim 10, wherein the carotenoid is β-carotene.

12. The composition as in claim 9, wherein the fat-soluble vitamin is Vitamin A or E.

13. The composition as in claim 8, wherein at least one compound selected from the group consisting of monosaccharides, disaccharides, oligosaccharides, polysaccharides, glycerol, triglycerides, water-soluble antioxidants and fat-soluble antioxidants is additionally present.

14. The composition as in claim 13, wherein the mono- or disaccharide is sucrose, invert sugar, xylose, glucose, fructose, lactose, maltose, saccharose and sugar alcohols.

15. The composition as in claim 13, wherein the oligo- or polysaccharide is a starch, a starch hydrolysate or a modified starch.

16. The composition as in claim 15, wherein the starch hydrolysate is a dextrin, a malto-dextrin or a glucose syrup.

17. The composition as in claim 9, wherein the triglyceride is a vegetable oil or fat.

18. The composition as in claim 8, wherein a co-emulgator selected from the group consisting of mono- and diglycerides of fatty acids, polyglycerol esters of fatty acids, lecithins, and sorbitan monostearate is additionally present.

19. The composition as in claim 8, wherein the rice endosperm protein has an emulsion activity of ≥0.6.

20. The composition as in claim 8, wherein the amount of the rice endosperm protein which is partially reacted with glucose or Xanthan gum is from about 1 to about 70 weight-% and/or the amount of the fat-soluble active ingredient and/or the fat-soluble colorant is from about 0.1 to about 90 weight-%, based on the total amount of the composition.

21. The composition as in claim 8 in the form of a powder.

22. A process for the manufacture of a composition as claimed in claim 8 which comprises the following steps:
   I) preparing an aqueous solution or colloidal solution of a rice endosperm protein which is partially reacted with glucose or Xanthan gum,
   II) optionally adding at least a water-soluble excipient and/or adjuvant to the solution prepared in step I),
   III) preparing a solution or dispersion of at least a fat-soluble active ingredient and/or a fat-soluble colorant, and optionally at least a fat-soluble adjuvant and/or excipient,
   (IV) mixing the solutions prepared in step I) to III) with each other,
   V) homogenising the thus resulting mixture,
   VI) optionally adding a cross-linking agent for further cross-linking the rice endosperm protein which is partially reacted with glucose or Xanthan gum,
   Via) optionally submitting the mixture resulting after having performed step VI) to enzymatic treatment or heat treatment to cross-link the (modified) rice endosperm protein
   VII) optionally converting the dispersion obtained in step V) and/or VI) into a powder,
   VIII) optionally drying the powder obtained in step VII),
   IX) optionally submitting the powder resulting from step VII or the dry powder resulting from step VIII to heat treatment or to enzymatic treatment to cross-link the rice endosperm protein which is partially reacted with glucose or Xanthan gum, wherein the enzymatic treatment according to step Via) or step 1x) is a treatment with transglutaminase,
   with the proviso that only step Via) or step 1x) is carried out, but not both, when step VI) is carried out.

23. The process according to claim 22 wherein the rice endosperm protein which is partially reacted with glucose or Xanthan gum is one as defined in claim 8.

24. A process for the enrichment, fortification and/or coloration of food, beverages, animal feed, personal care or pharmaceutical compositions whereby a composition as claimed in claim 8 is added to the food, beverages, animal feed, personal care compositions, respectively.

25. Food, beverages, animal feed, personal care and pharmaceutical compositions containing a composition as claimed in claim 8.

26. A process for the protection of fat-soluble active ingredients and/or fat-soluble colorants whereby the rice endosperm protein as claimed in claim 8 is added to said fat-soluble active ingredients and/or said fat soluble colorants as a protecting agent.

27. The composition as in claim 8, wherein the rice endosperm protein has an emulsion activity of ≥0.7.

28. The composition as in claim 8, wherein the rice endosperm protein has an emulsion stability of ≥23 minutes.

29. The composition as in claim 8, wherein the rice endosperm protein has an emulsion stability of ≥25 minutes.

30. Process for the enrichment, fortification and/or coloration of food, beverages, animal feed, personal care or pharmaceutical compositions, whereby a composition as claimed in claim 8 is added to the food, beverages, animal feed, personal care and pharmaceutical compositions, respectively.

31. A process for the manufacture of a rice endosperm protein which is partially conjugated with glucose or Xanthan gum, whereby before milling the rice bran was removed, comprising the following steps a) to e):
   a) preparing an aqueous solution or suspension of milled rice, whereby the rice bran was removed before milling, whereby the solution or suspension has a dry mass content of from 0.1 to 30 weight-%, based on the total amount of the aqueous solution or suspension;
   b) removing the protein part of the milled rice, whereby the rice bran was removed before milling, to obtain the protein part;
   c) modifying the protein part of the milled rice, whereby the rice bran was removed before milling, by reacting the protein part of the milled rice partially with glucose or Xanthan gum in a Maillard reaction to obtain protein part which is partially reacted with glucose or Xanthan gum;
   d) optionally isolating the protein part which is partially reacted with glucose or Xanthan gum;
   e) optionally converting the protein part which is partially reacted with glucose or Xanthan into a solid form.

* * * * *